US007261899B1

(12) United States Patent
Carlin et al.

(10) Patent No.: US 7,261,899 B1
(45) Date of Patent: Aug. 28, 2007

(54) METHOD OF PRODUCING THY A-STRAINS OF *VIBRIO CHOLERAE*, SUCH STRAINS AND THEIR USE

(75) Inventors: Nils Carlin, Hasselby (SE); Michael R. Lebens, Gothenburg (SE)

(73) Assignee: SBL Vaccin AB, Stockholm (SE)

( * ) Notice: Subject to any disclaimer, the term of this patent is extended or adjusted under 35 U.S.C. 154(b) by 0 days.

(21) Appl. No.: 09/700,712

(22) PCT Filed: May 21, 1999

(86) PCT No.: PCT/EP99/03509

§ 371 (c)(1),
(2), (4) Date: Nov. 13, 2001

(87) PCT Pub. No.: WO99/61634

PCT Pub. Date: Dec. 2, 2000

(30) Foreign Application Priority Data

May 26, 1998 (SE) .................................. 9801852

(51) Int. Cl.

| | |
|---|---|
| ***A61K 39/02*** | (2006.01) |
| ***A61K 39/00*** | (2006.01) |
| ***A01N 63/00*** | (2006.01) |
| ***C12N 15/74*** | (2006.01) |
| ***C12N 15/09*** | (2006.01) |
| ***C12P 21/04*** | (2006.01) |
| ***C12P 21/06*** | (2006.01) |

(52) U.S. Cl. ................. 424/200.1; 424/93.4; 424/93.2; 424/261.1; 424/234.1; 435/69.3; 435/69.1; 435/71.1; 435/69.7; 435/471

(58) Field of Classification Search ............... 435/69.3, 435/69.7, 471, 476, 462, 7.1; 424/93.4, 184.1, 424/200.1, 261.1, 234.1, 93.2
See application file for complete search history.

(56) References Cited

U.S. PATENT DOCUMENTS 5,198,343 A 3/1993 DeGryse .................... 435/69.1
5,434,065 A * 7/1995 Mahan et al. .................. 435/6
5,470,729 A 11/1995 Kaper et al. ............. 435/172.3
6,194,560 B1 * 2/2001 Arntzen et al. ............ 536/23.7
6,251,866 B1 * 6/2001 Prakash et al. ............... 514/17

FOREIGN PATENT DOCUMENTS

| | | | |
|---|---|---|---|
| EP | 0 251 579 A | 1/1988 |
| EP | 0 406 003 A | 1/1991 |
| GB | 2177097 A | 1/1987 |
| WO | WO94 19482 A | 9/1994 |
| WO | WO99 35271 A | 7/1999 |

OTHER PUBLICATIONS

Attridge et al. In: Proceed. Aust. Biotechnol. Conf. 8 Meeting. pp. 134-139, 1989.*
Valle et al. Infect. Immun. 68: 6411-6418, Nov. 1, 2000.*
Database EMPRO2 (Online), E.M.B.L. Databases Accession No. Y17135, May 1, 1998, Valle E. et al., "*Vibrio cholerae* thyA gene", XP002118053.
Attridge Sr: "Thymine auxotrophy as an attenuating marker in *Vibrio cholerae*", Microb Pathog, Jul. 1995, XP002118052.
Database EMPRO 2 (Online) E.M.B.L. Databases Accession No. AJ006514, Jun. 5, 1998, Carlin, N, "*Vibrio cholerae* Igt and thyA genes", XP002118055.
Database EMPRO2 (Online) E.M.B.L. Databases Accession No. AJ010968, Sep. 21, 1998, Carlin N. et al., "*Vibrio cholerage* nptA gene", XP002118054.

* cited by examiner

*Primary Examiner*—S. Devi
(74) *Attorney, Agent, or Firm*—Bacon & Thomas, PLLC

(57) ABSTRACT

A method of producing a thy $A^-$strain of *vibrio cholerae* comprising the step of site-directed mutagenesis in the *V. cholerae* chromosome at the locus of the thy A gene SEQ ID NO: 1 of FIG. 1, is described. Particularly, a Δ thy A strain of *Vibrio cholerae* lacking the functionality of the thy A is disclosed. This strain may comprise one or several episomal autonomously replicating DNA elements, such as plasmids, having an optionally foreign, e.g. *E. coli*, functional thy A gene that enables the strain to grow in the absence of thymine in the growth medium, and optionally having a structural gene encoding a homologous or heterologous protein. Further, proteins encoded by a structural thy A gene and the 5'-flanking region are described as SEQ ID NO: 4 of FIG. 4 and SEQ ID NO: 5 of FIG. 5, respectively. Additionally, a vaccine comprising a *Vibrio cholerae* Δ thy A strain of the invention or a thy $A^-$strain of *Vibrio cholerae* produced by the method of the invention is disclosed.

8 Claims, 18 Drawing Sheets

FIG. 1(a)

SEQ ID NO: 1:

GAGAAGGTTT GTTATGCCTC AGGGTTATCT GCAGTTTCCC AATATTGACC CCGTATTGTT 60

TTCGATCGGC CCTCTAGCGG TGCGCTGGTA TGGCTTGATG TATTTGGTGG GTTTCCTTTT 120

TGCTATGTGG TTGGCCAATC GCCGAGCGGA TCGCGCGGGC AGTGGTTGGA CGCGTGAGCA 180

AGTCTCTGAC TTGTTATTCG CCGGCTTTTT AGGTGTAGTG ATCGGTGGCC GAGTTGGTTA 240

TGTGATCTTC TACAATTTTG ATCTGTTCCT TGCTGACCCT CTTTATTTAT TCAAAGTGTG 300

GACTGGCGGC ATGTCCTTCC ACGGCGGCTT ATTGGGTGTG ATCACCGCCA TGTTCTGGTA 360

TGCGCGTAAA AACCAACGCA CCTTCTTTGG TGTGGCCGAT TTTGTTGCCC CTTTAGTGCC 420

ATTCGGTTTG GGGATGGGAC GTATCGGTAA. CTTTATGAAT AGTGAACTTT GGGGACGAGT 480

AACGGATGTG CCTTGGGCTT TTGTATTCCC TAATGGTGGC CCACTGCCGC GCCATCCTTC 540

ACAGCTTTAT GAATTCGCCT TAGAAGGCGT GGTTCTGTTC TTTATTCTTA ATTGGTTTAT 600

TGGTAAACCT CGTCCGCTAG GCAGCGTATC CGGACTGTTT TTAGCTGGAT ACGGTACATT 660

CCGCTTCCTT GTGGAATACG TCCGTGAGCC AGATGCTCAG TTGGGTCTGT TTGGTGGCTT 720

CATTTCAATG GGGCAAATCC TCTCCTTACC TATGGTGATC ATCGGTATTT TGATGATGGT 780

TTGGTCTTAC AAGCGCGGTT TGTATCAAGA CCGTGTAGCA GCAAAAATAGG GTAGTTAGGT 840

GAAACAGTAT TTAGATCTTT GTCAGCGCAT CGTCGATCAA GGTGTTTGGG TTGAAAATGA 900

ACGAACGGGC AAGCGTTGTT TGACTGTGAT TAATGCCGAT TTGACCTACG ATGTGGGCAA 960

CAATCAGTTT CCTCTAGTGA CTACACGCAA GAGTTTTTGG AAAGCTGCCG TAGCCGAGTT 1020

GCTCGGCTAT ATTCGTGGTT ACGATAATGC GGCGGATTTT CGCCAATTAG GTACCAAAAC 1080

CTGGGATGCT AATGCCAATT TAAACCAAGC ATGGCTCAAC AATCCTTACC GTAAAGGTGA 1140

GGATGACATG GGACGCGTGT ATGGTGTTCA GGGTAGAGCT TGGGCTAAGC CTGATGGTGG 1200

TCATATTGAC CAGTTGAAAA AGATTGTTGA TGATTTGAGC CGTGGCGTTG ATGACCGAGG 1260

TGAAATTCTT AACTTCTACA ATCCGGGTGA ATTTCACATG GGGTGTTTGC GCCCTTGCAT 1320

GTACAGCCAT CATTTTTCAT TGCTGGGGGA TACCTTGTAT CTCAACAGTA CTCAGCGTTC 1380

ATGTGATGTG CCCTTGGGGT TGAATTTCAA CATGGTGCAG GTTTATGTGT TCCTTGCGCT 1440

GATGGCACAG ATCACAGGGA AAAAGCCGGG CTTGGCGTAT CACAAGATCG TCAATGCGCA 1500

FIG. 1(b)

CATTTACCAA GATCAACTCG AATTGATGCG CGATGTGCAG CTAAAACGTG AGCCATTCCC 1560
AGCGCCTCAG TTCCATATCA ATCCAAAGAT TAAAACACTG CAGGATTTGG AAACTTGGGT 1620
CACTTTGGAT GATTTTGACG TCACCGGATA TCAGTTCCAC GATCCTATTC AATACCCGTT 1680
TTCAGTCTAA TCCCGTATTC AGGCGGTATG GCTTGATGGG TTTTATATAA AAAAAGCTCC 1740
CGAAGGTCGG GAGCTTTTTT TATACAGATG ATGCTTTAAC GCTTAAGCGG TTAGGGCAAG 1800
AATGCTGCCG GGGATGACGA CAAACACACC CAATAAGTAA CTCACCACCA CCATTTTGCT 1860
CTTACAAGCC CAAGTTGAGA TGAGCTCAGC ACCTTTAATA GGCAGTTCGC GTAAGAAAGG 1920
AATACCGTAA ATCAAGACCG TAGCCATCAA GTTAAAGCTT AAGTGCACCA GCGCAATTTG 1980
CAGAGCAAAC ACGGCAAACT CACCAGAGAC AGCGGTTGCG GCGAGCAGAG CAGTAATACA 2040
AGTGCCAATG TTCGCACCTA AGGTAAATGG GTAGATTTCA CGCACTTTCA GCACGCCAGA 2100
GCCCACGAGA GGAACCATTA GGCTGGTTGT GGTCGATGAA GATTGAACTA ATACCGTAAC 2160
CACTGTACCT GAAGCAATAC CGTGTAGTGG GCCTCGGCCA ATCGCATTTT GTAGAATTTC 2220
ACGTGCGCGG CCAACCATCA AACTCTTCAT CAGTTTGCCC ATCACCGTAA TGGCGACGAA 2280
AATGGTCGCA ATACCCAATA CGATAAGTGC GACACCACCG AAAGTATTAC CCAATACCGA 2340
AAGCTGGGTT TCAAGCCCTG TGATGACAGG TTTGGTAATC GGTTTGATAA AATCAAAACC 2400
TTTCATGCTC ATATCGCCAG TCGCAAGCAG AGGCGAAACG AGCCAGTGTG AGACTTTCTC 2460
TAAAATGCCA AACATCATTT CTAGAGGTAG GAAGATCAGC ACCGCGAGAA GATTGAAAAA 2520
ATCGTGGATG GTGGCACTGG CGAAAGCACG GCGAAACTCT TCTTTACAGC GCATATGGCC 2580
AAGGCTGACG AGAGTATTGG TCACAGTAGT ACCAATATTG GCACCCATCA CCATAGGAAT 2640
CGCGGTTTCA ACCGGTAACC CACCGGCAAC GAGACCAACA ATAATAGAAG TCACCGTGCT 2700
TGAGGATTGA ATCAGTGCCG TTGCCACTAA ACCAATCATC AATCCTGCAA TTGGGTGGGA 2760
AGCAAATTCA AATAGAACTT TGGCTTGATC GCCGGTTGCC CATTTAAAAC CGCTGCCGAC 2820
CATCGCGACT GCAAGAAGTA GTAAATACAG CATGAAAGCC AAGTTTGCCC AACGTAGGCC 2880
TTTCGTGGTC AGCGAAATCG GCGCTGCAG 2909

FIG.2

SEQ ID NO: 2:

```
GAGAAGGTTT GTTATGCCTC AGGGTTATCT GCAGTTTCCC AATATTGACC CCGTATTGTT    60
TTCGATCGGC CCTCTAGCGG TGCGCTGGTA TGGCTTGATG TATTTGGTGG GTTTCCTTTT   120
TGCTATGTGG TTGGCCAATC GCCGAGCGGA TCGCGCGGGC AGTGGTTGGA CGCGTGAGCA   180
AGTCTCTGAC TTGTTATTCG CCGGCTTTTT AGGTGTAGTG ATCGGTGGCC GAGTTGGTTA   240
TGTGATCTTC TACAATTTTG ATCTGTTCCT TGCTGACCCT CTTTATTTAT TCAAAGTGTG   300
GACTGGCGGC ATGTCCTTCC ACGGCGGCTT ATTGGGTGTG ATCACCGCCA TGTTCTGGTA   360
TGCGCGTAAA AACCAACGCA CCTTCTTTGG TGTGGCCGAT TTTGTTGCCC CTTTAGTGCC   420
ATTCGGTTTG GGGATGGGAC GTATCGGTAA CTTTATGAAT AGTGAACTTT GGGGACGAGT   480
AACGGATGTG CCTTGGGCTT TTGTATTCCC TAATGGTGGC CCACTGCCGC GCCATCCTTC   540
ACAGCTTTAT GAATTCGCCT TAGAAGGCGT GGTTCTGTTC TTTATTCTTA ATTGGTTTAT   600
TGGTAAACCT CGTCCGCTAG GCAGCGTATC CGGACTGTTT TTAGCTGGAT ACGGTACATT   660
CCGCTTCCTT GTGGAATACG TCCGTGAGCC AGATGCTCAG TTGGGTCTGT TTGGTGGCTT   720
CATTTCAATG GGGCAAATCC TCTCCTTACC TATGGTGATC ATCGGTATTT TGATGATGGT   780
TTGGTCTTAC AAGCGCGGTT TGTATCAAGA CCGTGTAGCA GCAAAATAGG GTAGTTAG     838
```

FIG.3

SEQ ID NO: 3:

```
TAATCCCGTA TTCAGGCGGT ATGGCTTGAT GGGTTTTATA TAAAAAAAGC TCCCGAAGGT   60
CGGGAGCTTT TTTTATACAG ATGATGCTTT AACGCTTAAG CGGTTAGGGC AAGAATGCTG  120
CCGGGGATGA CGACAAACAC ACCCAATAAG TAACTCACCA CCACCATTTT GCTCTTACAA  180
GCCCAAGTTG AGATGAGCTC AGCACCTTTA ATAGGCAGTT CGCGTAAGAA AGGAATACCG  240
TAAATCAAGA CCGTAGCCAT CAAGTTAAAG CTTAAGTGCA CCAGCGCAAT TTGCAGAGCA  300
AACACGGCAA ACTCACCAGA GACAGCGGTT GCGGCGAGCA GAGCAGTAAT ACAAGTGCCA  360
ATGTTCGCAC CTAAGGTAAA TGGGTAGATT TCACGCACTT TCAGCACGCC AGAGCCCACG  420
AGAGGAACCA TTAGGCTGGT TGTGGTCGAT GAAGATTGAA CTAATACCGT AACCACTGTA  480
CCTGAAGCAA TACCGTGTAG TGGGCCTCGG CCAATCGCAT TTTGTAGAAT TTCACGTGCG  540
CGGCCAACCA TCAAACTCTT CATCAGTTTG CCCATCACCG TAATGGCGAC GAAAATGGTC  600
GCAATACCCA ATACGATAAG TGCGACACCA CCGAAAGTAT TACCCAATAC CGAAAGCTGG  660
GTTTCAAGCC CTGTGATGAC AGGTTTGGTA ATCGGTTTGA TAAAATCAAA ACCTTTCATG  720
CTCATATCGC CAGTCGCAAG CAGAGGCGAA ACGAGCCAGT GTGAGACTTT CTCTAAAATG  780
CCAAACATCA TTTCTAGAGG TAGGAAGATC AGCACCGCGA GAAGATTGAA AAAATCGTGG  840
ATGGTGGCAC TGGCGAAAGC ACGGCGAAAC TCTTCTTTAC AGCGCATATG GCCAAGGCTG  900
ACGAGAGTAT TGGTCACAGT AGTACCAATA TTGGCACCCA TCACCATAGG AATCGCGGTT  960
TCAACCGGTA ACCCACCGGC AACGAGACCA ACAATAATAG AAGTCACCGT GCTTGAGGAT 1020
TGAATCAGTG CCGTTGCCAC TAAACCAATC ATCAATCCTG CAATTGGGTG GGAAGCAAAT 1080
TCAAATAGAA CTTTGGCTTG ATCGCCGGTT GCCCATTTAA AACCGCTGCC GACCATCGCG 1140
ACTGCAAGAA GTAGTAAATA CAGCATGAAA GCCAAGTTTG CCCAACGTAG GCCTTTCGTG 1200
GTCAGCGAAA TCGGCGCTGC AG                                          1222
```

FIG.4

SEQ ID NO: 4:

```
Val Lys Gln Tyr Leu Asp Leu Cys Gln Arg Ile Val Asp Gln Gly Val
1               5                   10                  15

Trp Val Glu Asn Glu Arg Thr Gly Lys Arg Cys Leu Thr Val Ile Asn
            20                  25                  30

Ala Asp Leu Thr Tyr Asp Val Gly Asn Asn Gln Phe Pro Leu Val Thr
        35                  40                  45

Thr Arg Lys Ser Phe Trp Lys Ala Ala Val Ala Glu Leu Leu Gly Tyr
    50                  55                  60

Ile Arg Gly Tyr Asp Asn Ala Ala Asp Phe Arg Gln Leu Gly Thr Lys
65                  70                  75                  80

Thr Trp Asp Ala Asn Ala Asn Leu Asn Gln Ala Trp Leu Asn Asn Pro
                85                  90                  95

Tyr Arg Lys Gly Glu Asp Asp Met Gly Arg Val Tyr Gly Val Gln Gly
            100                 105                 110

Arg Ala Trp Ala Lys Pro Asp Gly Gly His Ile Asp Gln Leu Lys Lys
        115                 120                 125

Ile Val Asp Asp Leu Ser Arg Gly Val Asp Asp Arg Gly Glu Ile Leu
    130                 135                 140

Asn Phe Tyr Asn Pro Gly Glu Phe His Met Gly Cys Leu Arg Pro Cys
145                 150                 155                 160

Met Tyr Ser His His Phe Ser Leu Leu Gly Asp Thr Leu Tyr Leu Asn
                165                 170                 175

Ser Thr Gln Arg Ser Cys Asp Val Pro Leu Gly Leu Asn Phe Asn Met
            180                 185                 190

Val Gln Val Tyr Val Phe Leu Ala Leu Met Ala Gln Ile Thr Gly Lys
        195                 200                 205

Lys Pro Gly Leu Ala Tyr His Lys Ile Val Asn Ala His Ile Tyr Gln
    210                 215                 220

Asp Gln Leu Glu Leu Met Arg Asp Val Gln Leu Lys Arg Glu Pro Phe
225                 230                 235                 240

Pro Ala Pro Gln Phe His Ile Asn Pro Lys Ile Lys Thr Leu Gln Asp
                245                 250                 255

Leu Glu Thr Trp Val Thr Leu Asp Asp Phe Asp Val Thr Gly Tyr Gln
            260                 265                 270

Phe His Asp Pro Ile Gln Tyr Pro Phe Ser Val
        275                 280
```

FIG. 5

SEQ ID NO: 5:

```
Met Pro Gln Gly Tyr Leu Gln Phe Pro Asn Ile Asp Pro Val Leu Phe
1               5                   10                  15

Ser Ile Gly Pro Leu Ala Val Arg Trp Tyr Gly Leu Met Tyr Leu Val
            20                  25                  30

Gly Phe Leu Phe Ala Met Trp Leu Ala Asn Arg Arg Ala Asp Arg Ala
        35                  40                  45

Gly Ser Gly Trp Thr Arg Glu Gln Val Ser Asp Leu Leu Phe Ala Gly
    50                  55                  60

Phe Leu Gly Val Val Ile Gly Gly Arg Val Gly Tyr Val Ile Phe Tyr
65                  70                  75                  80

Asn Phe Asp Leu Phe Leu Ala Asp Pro Leu Tyr Leu Phe Lys Val Trp
                85                  90                  95

Thr Gly Gly Met Ser Phe His Gly Gly Leu Leu Gly Val Ile Thr Ala
            100                 105                 110

Met Phe Trp Tyr Ala Arg Lys Asn Gln Arg Thr Phe Phe Gly Val Ala
        115                 120                 125

Asp Phe Val Ala Pro Leu Val Pro Phe Gly Leu Gly Met Gly Arg Ile
    130                 135                 140

Gly Asn Phe Met Asn Ser Glu Leu Trp Gly Arg Val Thr Asp Val Pro
145                 150                 155                 160

Trp Ala Phe Val Phe Pro Asn Gly Gly Pro Leu Pro Arg His Pro Ser
                165                 170                 175

Gln Leu Tyr Glu Phe Ala Leu Glu Gly Val Val Leu Phe Phe Ile Leu
            180                 185                 190

Asn Trp Phe Ile Gly Lys Pro Arg Pro Leu Gly Ser Val Ser Gly Leu
        195                 200                 205

Phe Leu Ala Gly Tyr Gly Thr Phe Arg Phe Leu Val Glu Tyr Val Arg
    210                 215                 220

Glu Pro Asp Ala Gln Leu Gly Leu Phe Gly Gly Phe Ile Ser Met Gly
225                 230                 235                 240

Gln Ile Leu Ser Leu Pro Met Val Ile Ile Gly Ile Leu Met Met Val
                245                 250                 255

Trp Ser Tyr Lys Arg Gly Leu Tyr Gln Asp Arg Val Ala Ala Lys
            260                 265                 270
```

FIG. 7

```
E. coli     : MKQYLELMQKVLDEGT-QKNDRTGTGTLSIFGHQMRFNL-QDGFPLVTTKRCHLRSIIHE
              :||||:| |:::|:|:  :|:|||:  |:::: :: ::: :: ||||||:::  :: : |
V. cholerae : VKQYLDLCQRIVDQGVWVENERTGKRCLTVINADLTYDVGNNQFPLVTTRKSFWKAAVAE
              :||||:||:|||::| ||:||||||:|||||||||:|||:||||||:|||||:||||:||
H. influenza: MKQYLELCRRIVSEGEWVANERTGKHCLTVINADLEYDVANNQFPLITTRKSYWKAAIAE

E. coli     : LLWFLQGDTNIAYHENNVTIWD--------EWADE-----NGDLGPVYGKQWRAWPTPDG
              || :::| :| | ::: :::||        :| ::      ::|:|:||| | |||::|||
V. cholerae : LLGYIRGYDNAADFRQLGTKTWDANANLNQAWLNNPYRKGEDDMGRVYGVQGRAWAKPDG
              :||||||||||||||:|||||||||||| |:|||:||:|:|:| |||||||||||| ||:|
H. influenza: FLGYIRGYDNAADFRALGTKTWDANANENAAWLANPHRRGVDDMGRVYGVQGRAWRKPNG

E. coli     : RHIDQITTVLNQLKNDPDSRRIIVSAWNVGELDKMALAPCHAFFQFYVADGKLSCQLYQR
               ||||:::::::|::: |:|  |:: :| ||:::   | ||      :| : :::|  :  ||
V. cholerae : GHIDQLKKIVDDLSRGVDDRGEILNFYNPGEFHMGCLRPCMYSHHFSLLGDTLYLNSTQR
              : ||||:|||::|::|:||||||||:|:|||||::||||||||::| |||:||||:|:| ||
H. influenza: ETIDQLRKIVNNLTKGIDDRGEILTFFNPGEFDLGCLRPCMHTHTFSLVGDTLHLTSYQR

E. coli     : SCDVFLGLPFNIASYALLVHMMAQQCDLEVGDFVWTGGDTHLYSNHMD-QTHLQLSREPR
              |||| ||| ||::    ::: :|||   : : |     :   ::|:| ::::    ::||:|||
V. cholerae : SCDVPLGLNFNMVQVYVFLALMAQITGKKPGLAYHKIVNAHIYQDQLELMRDVQLKREPF
              ||||||||||| :||::|||||||||||||:| ||||||||||:||||||||||||||||
H. influenza: SCDVPLGLNFNQIQVFTFLALMAQITGKKAGKAYHKIVNAHIYEDQLELMRDVQLKREPF

E. coli     : PLPKLIIKRKPESIFDY----RFEDFEIEGYDPHPGIKAPVAI (SEQ ID NO:6)
              | |:: |::| ::: |        ::||:::||: |  |: | ::
V. cholerae : PAPQFHINPKIKTLQDLETWVTLDDFDVTGYQFHDPIQYPFSV (SEQ ID NO:4)
              | |:::||||||||||||||||||||||||||||||||||||||
H. influenza: PLPKELINPDIKTLEDLETWVTMDDFKVVGYQSHEPIKYPFSV (SEQ ID NO:7)
```

PCR to generate thyA-Kan-thyA fragment with *Xba*I ends. Primers were choosen so that the *Eco*RI and *Hind*III sites were eliminated thyA with kan XbaI ends
(2643 bp)

SEQUENCE LISTING

```
<160> NUMBER OF SEQ ID NOS: 15

<210> SEQ ID NO 1
<211> LENGTH: 2909
<212> TYPE: DNA
<213> ORGANISM: Vibrio cholerae

<400> SEQUENCE: 1

gagaaggttt gttatgcctc agggttatct gcagtttccc aatattgacc ccgtattgtt      60

ttcgatcggc cctctagcgg tgcgctggta tggcttgatg tatttggtgg gtttcctttt     120

tgctatgtgg ttggccaatc gccgagcgga tcgcgcgggc agtggttgga cgcgtgagca     180

agtctctgac ttgttattcg ccggcttttt aggtgtagtg atcggtggcc gagttggtta     240

tgtgatcttc tacaattttg atctgttcct tgctgaccct ctttatttat tcaaagtgtg     300

gactggcggc atgtccttcc acggcggctt attgggtgtg atcaccgcca tgttctggta     360

tgcgcgtaaa aaccaacgca ccttctttgg tgtggccgat tttgttgccc ctttagtgcc     420

attcggtttg gggatgggac gtatcggtaa ctttatgaat agtgaacttt ggggacgagt     480
```

-continued

```
aacggatgtg ccttgggctt ttgtattccc taatggtggc ccactgccgc gccatccttc    540
acagctttat gaattcgcct tagaaggcgt ggttctgttc tttattctta attggtttat    600
tggtaaacct cgtccgctag gcagcgtatc cggactgttt ttagctggat acggtacatt    660
ccgcttcctt gtggaatacg tccgtgagcc agatgctcag ttgggtctgt ttggtggctt    720
catttcaatg gggcaaatcc tctccttacc tatggtgatc atcggtattt tgatgatggt    780
ttggtcttac aagcgcggtt tgtatcaaga ccgtgtagca gcaaaatagg gtagttaggt    840
gaaacagtat ttagatcttt gtcagcgcat cgtcgatcaa ggtgtttggg ttgaaaatga    900
acgaacgggc aagcgttgtt tgactgtgat taatgccgat ttgacctacg atgtgggcaa    960
caatcagttt cctctagtga ctacacgcaa gagtttttgg aaagctgccg tagccgagtt   1020
gctcggctat attcgtggtt acgataatgc ggcggatttt cgccaattag gtaccaaaac   1080
ctgggatgct aatgccaatt taaaccaagc atggctcaac aatccttacc gtaaaggtga   1140
ggatgacatg ggacgcgtgt atggtgttca gggtagagct tgggctaagc ctgatggtgg   1200
tcatattgac cagttgaaaa agattgttga tgatttgagc cgtggcgttg atgaccgagg   1260
tgaaattctt aacttctaca atccgggtga atttcacatg ggtgtttgc gcccttgcat   1320
gtacagccat catttttcat tgctggggga taccttgtat ctcaacagta ctcagcgttc   1380
atgtgatgtg cccttggggt tgaatttcaa catggtgcag gtttatgtgt tccttgcgct   1440
gatggcacag atcacaggga aaaagccggg cttggcgtat cacaagatcg tcaatgcgca   1500
catttaccaa gatcaactcg aattgatgcg cgatgtgcag ctaaaacgtg agccattccc   1560
agcgcctcag ttccatatca atccaaagat taaaacactg caggatttgg aaacttgggt   1620
cactttggat gattttgacg tcaccggata tcagttccac gatcctattc aatacccgtt   1680
ttcagtctaa tcccgtattc aggcggtatg gcttgatggg ttttatataa aaaaagctcc   1740
cgaaggtcgg gagctttttt tatacagatg atgctttaac gcttaagcgg ttagggcaag   1800
aatgctgccg gggatgacga caaacacacc caataagtaa ctcaccacca ccattttgct   1860
cttacaagcc caagttgaga tgagctcagc acctttaata ggcagttcgc gtaagaaagg   1920
aataccgtaa atcaagaccg tagccatcaa gttaaagctt aagtgcacca gcgcaatttg   1980
cagagcaaac acggcaaact caccagagac agcggttgcg gcgagcagag cagtaataca   2040
agtgccaatg ttcgcaccta aggtaaatgg gtagatttca cgcactttca gcacgccaga   2100
gcccacgaga ggaaccatta ggctggttgt ggtcgatgaa gattgaacta ataccgtaac   2160
cactgtacct gaagcaatac cgtgtagtgg gcctcggcca atcgcatttt gtagaatttc   2220
acgtgcgcgg ccaaccatca aactcttcat cagtttgccc atcaccgtaa tggcgacgaa   2280
aatggtcgca atacccaata cgataagtgc gacaccaccg aaagtattac ccaataccga   2340
aagctgggtt tcaagccctg tgatgacagg tttggtaatc ggtttgataa aatcaaaacc   2400
tttcatgctc atatcgccag tcgcaagcag aggcgaaacg agccagtgtg agactttctc   2460
taaaatgcca aacatcattt ctagaggtag gaagatcagc accgcgagaa gattgaaaaa   2520
atcgtggatg gtggcactgg cgaaagcacg gcgaaactct tctttacagc gcatatggcc   2580
aaggctgacg agagtattgg tcacagtagt accaatattg gcacccatca ccataggaat   2640
cgcggtttca accggtaacc caccggcaac gagaccaaca ataatagaag tcaccgtgct   2700
tgaggattga atcagtgccg ttgccactaa accaatcatc aatcctgcaa ttgggtggga   2760
agcaaattca aatagaactt tggcttgatc gccggttgcc catttaaaac cgctgccgac   2820
```

-continued

```
catcgcgact gcaagaagta gtaaatacag catgaaagcc aagtttgccc aacgtaggcc   2880

tttcgtggtc agcgaaatcg gcgctgcag                                     2909


<210> SEQ ID NO 2
<211> LENGTH: 838
<212> TYPE: DNA
<213> ORGANISM: Vibrio cholerae

<400> SEQUENCE: 2

gagaaggttt gttatgcctc agggttatct gcagtttccc aatattgacc ccgtattgtt     60

ttcgatcggc cctctagcgg tgcgctggta tggcttgatg tatttggtgg gtttcctttt    120

tgctatgtgg ttggccaatc gccgagcgga tcgcgcgggc agtggttgga cgcgtgagca    180

agtctctgac ttgttattcg ccggcttttt aggtgtagtg atcggtggcc gagttggtta    240

tgtgatcttc tacaattttg atctgttcct tgctgaccct ctttatttat tcaaagtgtg    300

gactggcggc atgtccttcc acggcggctt attgggtgtg atcaccgcca tgttctggta    360

tgcgcgtaaa aaccaacgca ccttctttgg tgtggccgat tttgttgccc ctttagtgcc    420

attcggtttg gggatgggac gtatcggtaa ctttatgaat agtgaacttt ggggacgagt    480

aacggatgtg ccttgggctt ttgtattccc taatggtggc ccactgccgc gccatccttc    540

acagctttat gaattcgcct tagaaggcgt ggttctgttc tttattctta attggtttat    600

tggtaaacct cgtccgctag gcagcgtatc cggactgttt ttagctggat acggtacatt    660

ccgcttcctt gtggaatacg tccgtgagcc agatgctcag ttgggtctgt ttggtggctt    720

catttcaatg gggcaaatcc tctccttacc tatggtgatc atcggtattt tgatgatggt    780

ttggtcttac aagcgcggtt tgtatcaaga ccgtgtagca gcaaaatagg gtagttag      838


<210> SEQ ID NO 3
<211> LENGTH: 1222
<212> TYPE: DNA
<213> ORGANISM: Vibrio cholerae

<400> SEQUENCE: 3

taatcccgta ttcaggcggt atggcttgat gggttttata taaaaaaagc tcccgaaggt     60

cgggagcttt ttttatacag atgatgcttt aacgcttaag cggttagggc aagaatgctg    120

ccggggatga cgacaaacac acccaataag taactcacca ccaccatttt gctcttacaa    180

gcccaagttg agatgagctc agcaccttta ataggcagtt cgcgtaagaa aggaataccg    240

taaatcaaga ccgtagccat caagttaaag cttaagtgca ccagcgcaat ttgcagagca    300

aacacggcaa actcaccaga gacagcggtt gcggcgagca gagcagtaat acaagtgcca    360

atgttcgcac ctaaggtaaa tgggtagatt tcacgcactt tcagcacgcc agagcccacg    420

agaggaacca ttaggctggt tgtggtcgat gaagattgaa ctaataccgt aaccactgta    480

cctgaagcaa taccgtgtag tgggcctcgg ccaatcgcat tttgtagaat ttcacgtgcg    540

cggccaacca tcaaactctt catcagtttg cccatcaccg taatggcgac gaaaatggtc    600

gcaataccca atacgataag tgcgacacca ccgaaagtat tacccaatac cgaaagctgg    660

gtttcaagcc ctgtgatgac aggtttggta atcggtttga taaaatcaaa acctttcatg    720

ctcatatcgc cagtcgcaag cagaggcgaa acgagccagt gtgagacttt ctctaaaatg    780

ccaaacatca tttctagagg taggaagatc agcaccgcga gaagattgaa aaaatcgtgg    840

atggtggcac tggcgaaagc acggcgaaac tcttctttac agcgcatatg gccaaggctg    900

acgagagtat tggtcacagt agtaccaata ttggcaccca tcaccatagg aatcgcggtt    960
```

-continued

```
tcaaccggta acccaccggc aacgagacca acaataatag aagtcaccgt gcttgaggat   1020

tgaatcagtg ccgttgccac taaaccaatc atcaatcctg caattgggtg ggaagcaaat   1080

tcaaatagaa ctttggcttg atcgccggtt gcccatttaa aaccgctgcc gaccatcgcg   1140

actgcaagaa gtagtaaata cagcatgaaa gccaagtttg cccaacgtag gcctttcgtg   1200

gtcagcgaaa tcggcgctgc ag                                            1222


<210> SEQ ID NO 4
<211> LENGTH: 283
<212> TYPE: PRT
<213> ORGANISM: Vibrio cholerae

<400> SEQUENCE: 4

Val Lys Gln Tyr Leu Asp Leu Cys Gln Arg Ile Val Asp Gln Gly Val
1               5                   10                  15

Trp Val Glu Asn Glu Arg Thr Gly Lys Arg Cys Leu Thr Val Ile Asn
            20                  25                  30

Ala Asp Leu Thr Tyr Asp Val Gly Asn Asn Gln Phe Pro Leu Val Thr
        35                  40                  45

Thr Arg Lys Ser Phe Trp Lys Ala Ala Val Ala Glu Leu Leu Gly Tyr
    50                  55                  60

Ile Arg Gly Tyr Asp Asn Ala Ala Asp Phe Arg Gln Leu Gly Thr Lys
65                  70                  75                  80

Thr Trp Asp Ala Asn Ala Asn Leu Asn Gln Ala Trp Leu Asn Asn Pro
                85                  90                  95

Tyr Arg Lys Gly Glu Asp Asp Met Gly Arg Val Tyr Gly Val Gln Gly
            100                 105                 110

Arg Ala Trp Ala Lys Pro Asp Gly Gly His Ile Asp Gln Leu Lys Lys
        115                 120                 125

Ile Val Asp Asp Leu Ser Arg Gly Val Asp Asp Arg Gly Glu Ile Leu
    130                 135                 140

Asn Phe Tyr Asn Pro Gly Glu Phe His Met Gly Cys Leu Arg Pro Cys
145                 150                 155                 160

Met Tyr Ser His His Phe Ser Leu Leu Gly Asp Thr Leu Tyr Leu Asn
                165                 170                 175

Ser Thr Gln Arg Ser Cys Asp Val Pro Leu Gly Leu Asn Phe Asn Met
            180                 185                 190

Val Gln Val Tyr Val Phe Leu Ala Leu Met Ala Gln Ile Thr Gly Lys
        195                 200                 205

Lys Pro Gly Leu Ala Tyr His Lys Ile Val Asn Ala His Ile Tyr Gln
    210                 215                 220

Asp Gln Leu Glu Leu Met Arg Asp Val Gln Leu Lys Arg Glu Pro Phe
225                 230                 235                 240

Pro Ala Pro Gln Phe His Ile Asn Pro Lys Ile Lys Thr Leu Gln Asp
                245                 250                 255

Leu Glu Thr Trp Val Thr Leu Asp Asp Phe Asp Val Thr Gly Tyr Gln
            260                 265                 270

Phe His Asp Pro Ile Gln Tyr Pro Phe Ser Val
        275                 280


<210> SEQ ID NO 5
<211> LENGTH: 271
<212> TYPE: PRT
<213> ORGANISM: Vibrio cholerae
```

-continued

<400> SEQUENCE: 5

```
Met Pro Gln Gly Tyr Leu Gln Phe Pro Asn Ile Asp Pro Val Leu Phe
1               5                   10                  15

Ser Ile Gly Pro Leu Ala Val Arg Trp Tyr Gly Leu Met Tyr Leu Val
            20                  25                  30

Gly Phe Leu Phe Ala Met Trp Leu Ala Asn Arg Arg Ala Asp Arg Ala
        35                  40                  45

Gly Ser Gly Trp Thr Arg Glu Gln Val Ser Asp Leu Leu Phe Ala Gly
    50                  55                  60

Phe Leu Gly Val Val Ile Gly Gly Arg Val Gly Tyr Val Ile Phe Tyr
65                  70                  75                  80

Asn Phe Asp Leu Phe Leu Ala Asp Pro Leu Tyr Leu Phe Lys Val Trp
                85                  90                  95

Thr Gly Gly Met Ser Phe His Gly Gly Leu Leu Gly Val Ile Thr Ala
            100                 105                 110

Met Phe Trp Tyr Ala Arg Lys Asn Gln Arg Thr Phe Phe Gly Val Ala
        115                 120                 125

Asp Phe Val Ala Pro Leu Val Pro Phe Gly Leu Gly Met Gly Arg Ile
    130                 135                 140

Gly Asn Phe Met Asn Ser Glu Leu Trp Gly Arg Val Thr Asp Val Pro
145                 150                 155                 160

Trp Ala Phe Val Phe Pro Asn Gly Gly Pro Leu Pro Arg His Pro Ser
                165                 170                 175

Gln Leu Tyr Glu Phe Ala Leu Glu Gly Val Val Leu Phe Phe Ile Leu
            180                 185                 190

Asn Trp Phe Ile Gly Lys Pro Arg Pro Leu Gly Ser Val Ser Gly Leu
        195                 200                 205

Phe Leu Ala Gly Tyr Gly Thr Phe Arg Phe Leu Val Glu Tyr Val Arg
    210                 215                 220

Glu Pro Asp Ala Gln Leu Gly Leu Phe Gly Gly Phe Ile Ser Met Gly
225                 230                 235                 240

Gln Ile Leu Ser Leu Pro Met Val Ile Ile Gly Ile Leu Met Met Val
                245                 250                 255

Trp Ser Tyr Lys Arg Gly Leu Tyr Gln Asp Arg Val Ala Ala Lys
            260                 265                 270
```

<210> SEQ ID NO 6
<211> LENGTH: 263
<212> TYPE: PRT
<213> ORGANISM: Escherichia coli

<400> SEQUENCE: 6

```
Met Lys Gln Tyr Leu Glu Leu Met Gln Lys Val Leu Asp Glu Gly Thr
1               5                   10                  15

Gln Lys Asn Asp Arg Thr Gly Thr Gly Thr Leu Ser Ile Phe Gly His
            20                  25                  30

Gln Met Arg Phe Asn Leu Gln Asp Gly Phe Pro Leu Val Thr Thr Lys
        35                  40                  45

Arg Cys His Leu Arg Ser Ile Ile His Glu Leu Leu Trp Phe Leu Gln
    50                  55                  60

Gly Asp Thr Asn Ile Ala Tyr His Glu Asn Asn Val Thr Ile Trp Asp
65                  70                  75                  80

Glu Trp Ala Asp Glu Asn Gly Asp Leu Gly Pro Val Tyr Gly Lys Gln
                85                  90                  95
```

-continued

```
Trp Arg Ala Trp Pro Thr Pro Asp Gly Arg His Ile Asp Gln Ile Thr
            100                 105                 110

Thr Val Leu Asn Gln Leu Lys Asn Asp Pro Asp Ser Arg Arg Ile Ile
        115                 120                 125

Val Ser Ala Trp Asn Val Gly Glu Leu Asp Lys Met Ala Leu Ala Pro
    130                 135                 140

Cys His Ala Phe Phe Gln Phe Tyr Val Ala Asp Gly Lys Leu Ser Cys
145                 150                 155                 160

Gln Leu Tyr Gln Arg Ser Cys Asp Val Phe Leu Gly Leu Pro Phe Asn
                165                 170                 175

Ile Ala Ser Tyr Ala Leu Leu Val His Met Met Ala Gln Gln Cys Asp
            180                 185                 190

Leu Glu Val Gly Asp Phe Val Trp Thr Gly Gly Asp Thr His Leu Tyr
        195                 200                 205

Ser Asn His Met Asp Gln Thr His Leu Gln Leu Ser Arg Glu Pro Arg
    210                 215                 220

Pro Leu Pro Lys Leu Ile Ile Lys Arg Lys Pro Glu Ser Ile Phe Asp
225                 230                 235                 240

Tyr Arg Phe Glu Asp Phe Glu Ile Glu Gly Tyr Asp Pro His Pro Gly
                245                 250                 255

Ile Lys Ala Pro Val Ala Ile
            260


<210> SEQ ID NO 7
<211> LENGTH: 283
<212> TYPE: PRT
<213> ORGANISM: Haemophilus influenzae

<400> SEQUENCE: 7

Met Lys Gln Tyr Leu Glu Leu Cys Arg Arg Ile Val Ser Glu Gly Glu
1               5                   10                  15

Trp Val Ala Asn Glu Arg Thr Gly Lys His Cys Leu Thr Val Ile Asn
            20                  25                  30

Ala Asp Leu Glu Tyr Asp Val Ala Asn Asn Gln Phe Pro Leu Ile Thr
        35                  40                  45

Thr Arg Lys Ser Tyr Trp Lys Ala Ala Ile Ala Glu Phe Leu Gly Tyr
    50                  55                  60

Ile Arg Gly Tyr Asp Asn Ala Ala Asp Phe Arg Ala Leu Gly Thr Lys
65                  70                  75                  80

Thr Trp Asp Ala Asn Ala Asn Glu Asn Ala Ala Trp Leu Ala Asn Pro
                85                  90                  95

His Arg Arg Gly Val Asp Asp Met Gly Arg Val Tyr Gly Val Gln Gly
            100                 105                 110

Arg Ala Trp Arg Lys Pro Asn Gly Glu Thr Ile Asp Gln Leu Arg Lys
        115                 120                 125

Ile Val Asn Asn Leu Thr Lys Gly Ile Asp Asp Arg Gly Glu Ile Leu
    130                 135                 140

Thr Phe Phe Asn Pro Gly Glu Phe Asp Leu Gly Cys Leu Arg Pro Cys
145                 150                 155                 160

Met His Thr His Thr Phe Ser Leu Val Gly Asp Thr Leu His Leu Thr
                165                 170                 175

Ser Tyr Gln Arg Ser Cys Asp Val Pro Leu Gly Leu Asn Phe Asn Gln
            180                 185                 190

Ile Gln Val Phe Thr Phe Leu Ala Leu Met Ala Gln Ile Thr Gly Lys
        195                 200                 205
```

```
Lys Ala Gly Lys Ala Tyr His Lys Ile Val Asn Ala His Ile Tyr Glu
    210                 215                 220

Asp Gln Leu Glu Leu Met Arg Asp Val Gln Leu Lys Arg Glu Pro Phe
225                 230                 235                 240

Pro Leu Pro Lys Leu Glu Ile Asn Pro Asp Ile Lys Thr Leu Glu Asp
                245                 250                 255

Leu Glu Thr Trp Val Thr Met Asp Asp Phe Lys Val Val Gly Tyr Gln
            260                 265                 270

Ser His Glu Pro Ile Lys Tyr Pro Phe Ser Val
        275                 280
```

<210> SEQ ID NO 8
<211> LENGTH: 27
<212> TYPE: DNA
<213> ORGANISM: Artificial
<220> FEATURE:
<223> OTHER INFORMATION: PCR primer

<400> SEQUENCE: 8
gctctagagc cttagaaggc gtggttc                                    27

<210> SEQ ID NO 9
<211> LENGTH: 31
<212> TYPE: DNA
<213> ORGANISM: Artificial
<220> FEATURE:
<223> OTHER INFORMATION: PCR primer

<400> SEQUENCE: 9
gctctagagc tacggtcttg atttacggta t                               31

<210> SEQ ID NO 10
<211> LENGTH: 27
<212> TYPE: DNA
<213> ORGANISM: Artificial
<220> FEATURE:
<223> OTHER INFORMATION: PCR primer

<400> SEQUENCE: 10
gggggctcga ggggcacatc acatgaa                                    27

<210> SEQ ID NO 11
<211> LENGTH: 30
<212> TYPE: DNA
<213> ORGANISM: Artificial
<220> FEATURE:
<223> OTHER INFORMATION: PCR primer

<400> SEQUENCE: 11
cccccctcga gcgccagagt tgtttctgaa                                 30

<210> SEQ ID NO 12
<211> LENGTH: 26
<212> TYPE: DNA
<213> ORGANISM: Artificial
<220> FEATURE:
<223> OTHER INFORMATION: PCR primer

<400> SEQUENCE: 12
ggactagtgg gtttcctttt tgctat                                     26

<210> SEQ ID NO 13
<211> LENGTH: 29

-continued

```
<212> TYPE: DNA
<213> ORGANISM: Artificial
<220> FEATURE:
<223> OTHER INFORMATION: PCR primer

<400> SEQUENCE: 13

ccccgctcga gaccctattt tgctgctac                                        29


<210> SEQ ID NO 14
<211> LENGTH: 27
<212> TYPE: DNA
<213> ORGANISM: Artificial
<220> FEATURE:
<223> OTHER INFORMATION: PCR primer

<400> SEQUENCE: 14

cggggtacct ggcttgatgg gttttat                                          27


<210> SEQ ID NO 15
<211> LENGTH: 26
<212> TYPE: DNA
<213> ORGANISM: Artificial
<220> FEATURE:
<223> OTHER INFORMATION: PCR primer

<400> SEQUENCE: 15

gaaggccttc gcctctgctt gcgact                                           26
```

METHOD OF PRODUCING THY A-STRAINS OF *VIBRIO CHOLERAE*, SUCH STRAINS AND THEIR USE

The present invention relates to a method of producing thy A$^-$ strains of *Vibrio cholerae*, such strains and their use. The invention particularly relates to a strain of *Vibrio cholerae* that has been deprived of its thy A gene in the chromosome, i.e. a Δ thy A strain lacking the functionality of the thy A gene. This strain may comprise one or several episomal autonomously replicating DNA elements, such as plasmids, having an optionally foreign, e.g. *E. coli*, functional thy A gene that enables the strain to grow in the absence of thymine in the growth medium, and optionally having a structural gene encoding a homologous or heterologous protein. The invention further relates to thy A nucleotide sequences and proteins encoded by them, and a vaccine comprising as an immunizing component a *Vibrio cholerae* Δ thy A strain of the invention or a thy A$^-$ strain of *V. cholerae* produced by the method of the invention.

BACKGROUND

The expression of recombinant genes in bacterial hosts is most often achieved by the introduction of episomal self-replicating elements (e.g. plasmids) that encode the structural gene of the protein of interest under the control of an appropriate promoter, into host bacteria. Such plasmids are most commonly maintained by the inclusion of selective marker genes that encode proteins that confer resistance to specific antibiotics (such as ampicillin, chloramphenicol, kanamycin, tetracycline etc.). They are then maintained in the host by addition of the appropriate antibiotic to the culture medium.

Stable maintenance of plasmids in host strains often requires the addition of the appropriate antibiotic selection without which they may segregate out giving rise to significant numbers of cells in any culture, that are devoid of plasmid and therefore cannot express the desired product.

However, the use of antibiotics in the production of recombinant proteins is undesirable for a number of reasons. Apart from the obvious increase in costs arising from the need to add them as a supplement to the growth medium, the use of antibiotics is considered a problem in the production of any recombinant protein intended for human or veterinary use. This is primarily for three reasons. Firstly, residual antibiotics can, in sensitive individuals, cause severe allergic reactions. Secondly, there is the possibility of selection for antibiotic resistant bacteria in the natural bacterial flora of those using the product, and finally, DNA encoding the antibiotic resistance may also be transferred to sensitive bacteria in individuals using the product, thereby also spreading undesired antibiotic resistance in a cohort.

There are already inventions dealing with this problem, one such is the par gene which will effectively kill all cells that do not retain a copy of the plasmid after each cell division [1].

Another patent application [2], which touches on the invention described herein, was based on the knowledge of the thyA DNA sequence in *E. coli*. The authors introduced the thyA gene on a plasmid but used host strains that were spontaneous thyA$^-$ mutants selected on the bases of trimethoprim resistance. Such mutants are not well defined (carrying point mutations or small deletions) and may revert to the wild-type (i.e. thyA$^+$) at unacceptably high frequencies. This would lead to that the host bacteria could eliminate the plasmid and hence lose, or not give consistent and reliable, production of the desired recombinant product. An additional problem with trimethoprim selection is the possibility that resulting thymine dependence may arise due to a mutation in the dihydrofolate reductase (folA) gene and hence not be complemented by a plasmid-borne thyA gene [3]. This patent application has been discontinued at least in Europe.

The use of *V. cholerae* for expression of recombinant genes has been shown to be advantageous over other prokaryotic expression systems in common use in that specific recombinant products may be produced in large quantities and secreted into the culture medium, thereby facilitating downstream purification procedures. This is in contrast to *E. coli* where the product often assembles in the periplasmic space [4]. One important factor endowing *V. cholerae* with this property is the eps genes in *V. cholerae* [5].

Thymidylate synthetase encoded by the thyA gene of *Escherichia coli* and other bacteria catalyses the methylation of deoxyuridylate (dUMP) to deoxythymidylate (dTMP) and is an essential enzyme in the biosynthesis of deoxyribothymidine triphosphate (dTTP) for incorporation into DNA. In the absence of this enzyme the bacteria become dependent upon an external source of thymine which is incorporated into dTTP by a salvage pathway encoded by the deo genes [6].

Spontaneous mutants that are thyA$^-$ can be readily isolated on the basis of trimethoprim resistance. This antibiotic inhibits tetrahydrofolate regeneration from dihydrofolate produced by thymidylate synthetase-catalysed dTMP synthesis. Thus, if the cells are thyA they become thymine dependent but no longer deplete the tetrahydrofolate pool in the presence of trimethoprim.

DESCRIPTION OF THE INVENTION

The present invention is, in its different aspects, based on the novel nucleotide sequence of the thyA gene in *Vibrio cholerae*. A useful application of the thyA gene is e.g. in maintenance of recombinant plasmids employed in the over-production of recombinant proteins in *V. cholerae*, and in the use of the sequence for insertion of foreign genes in a selectable and site-specific manner into the *V. cholerae* chromosome.

One aspect of the invention is directed to a method of producing a thy A$^-$ strain of *Vibrio cholerae* comprising the step of site-directed mutagenesis in the *V. cholerae* chromosome for the deletion and/or insertion of gene nucleotides at the locus of the thy A gene having essentially the nucleotide sequence SEQ ID NO: 1 of FIG. 1.

The expression "having essentially the nucleotide sequence" in this specification and claims is intended to comprise nucleotide sequences which have some natural or unnatural nucleotide extensions, truncations, deletions or additions that do not interfere with the natural function of the nucleotide sequence in question.

Another aspect of the invention is directed to a *Vibrio cholerae* thy A$^-$ strain which is a Δ thy A strain lacking the functionality of the thy A gene.

In an embodiment of this aspect of the invention the Δ thy A strain of *V. cholerae* comprises one or several episomal autonomously replicating DNA elements having a functional thy A gene that enables the strain to grow in the absence of thymine in the growth medium.

In a preferred embodiment the episomal autonomously replicating DNA element is a plasmid.

In another preferred embodiment the Δ thy A strain according to the invention comprises in an episomal autonomously replicating DNA element, especially a plasmid, a foreign thy A gene, such as an *E. coli* gene.

In a particularly preferred embodiment of this aspect of the invention the A thy A strain according to the invention comprises in one or several episomal autonomously replicating DNA elements, especially plasmids, in addition to a foreign thy A gene, such as an *E. coli* gene, also a structural gene encoding a homologous or heterologous protein, such as heat labile enterotoxin B-subunit of *Escherichia coli* (LTB) or *Schistosoma japonicum* glutathione S-transferase 26 kD protein (GST 26 kD).

A third aspect of the invention is directed to a nucleotide sequence of a 5'-flanking region of a structural thy A gene of *Vibrio cholerae* having essentially the nucleotide sequence SEQ ID NO: 2 of FIG. 2.

A fourth aspect of the invention is directed to a nucleotide sequence of a 3'-flanking region of a structural thy A gene of *Vibrio cholerae* having essentially the nucleotide sequence SEQ ID NO: 3 of FIG. 3.

The nucleotide sequence SEQ ID NO: 1, is useful for insertion of foreign genes in a selectable and site-specific manner into the *V. cholerae* chromosome, and for site-directed mutagenesis in the production of *Vibrio cholerae* thy $A^-$ strains.

A fifth aspect of the invention is directed to a protein encoded by a nucleotide sequence of a thy A gene of *Vibrio cholerae* according to the invention, such as a protein having the amino-acid sequence SEQ ID NO: 4 of FIG. 4.

A sixth aspect of the invention is directed to a protein encoded by a nucleotide sequence of a 5'-flanking region of a structural thy A gene of *Vibrio cholerae* according to the invention, such as the protein having the amino-acid sequence SEQ ID NO: 5 of FIG. 5.

The proteins according to the fifth and sixth aspect of the invention are each useful for research purposes, and potential targets for anti-microbial therapy.

A seventh aspect of the invention is directed to a vaccine comprising as an immunising component a *Vibrio cholerae* Δ thy A strain according to the invention or a thy $A^-$ strain of *Vibrio cholerae* produced by the method of the invention. The vaccine will be used for prophylactic and therapeutic treatment of cholera and optionally other infectious diseases, especially in cases where the used strain has been engineered to express foreign proteins. The vaccine will in addition to the immunising component(s) comprise a vehicle, such as physiological saline solution, and other components frequently used in vaccines such as buffers and adjuvants. Useful vehicles, buffers, adjuvants and other components are disclosed in e.g. the European and US Pharmacopoeia.

SHORT DESCRIPTION OF THE DRAWINGS

FIGS. 1*a* and 1*b* show the nucleotide sequence SEQ ID NO:1 of the thy A gene of *Vibrio cholerae.*

FIG. 2 shows the nucleotide sequence SEQ ID NO:2 of the 5'-flanking region of the structural thy A gene of *Vibrio cholerae.*

FIG. 3 shows the nucleotide sequence SEQ ID NO:3 of the 3'-flanking region of the structural thy A gene of *Vibrio cholerae.*

FIG. 4 shows the amino-acid sequence SEQ ID NO:4 of the protein encoded by the structural thy A gene of *Vibrio cholerae.*

FIG. 5 shows the amino-acid sequence SEQ ID NO:5 of the protein encoded by the 5'-flanking region of the structural thy A gene of *Vibrio cholerae.*

FIG. 7 shows a comparison of thyA gene products from *E. coli* (SEQ ID NO: 6 having 263 amino acids) [16], *V. cholerae* (SEQ ID NO:4 having 283 amino acids) and *H. influenzae* (SEQ ID NO: 7 having 283 amino acids) [17] showing the high degree of homology between *V. cholerae* and *H. influenzae* compared with *E. coli.*

Figure 8:
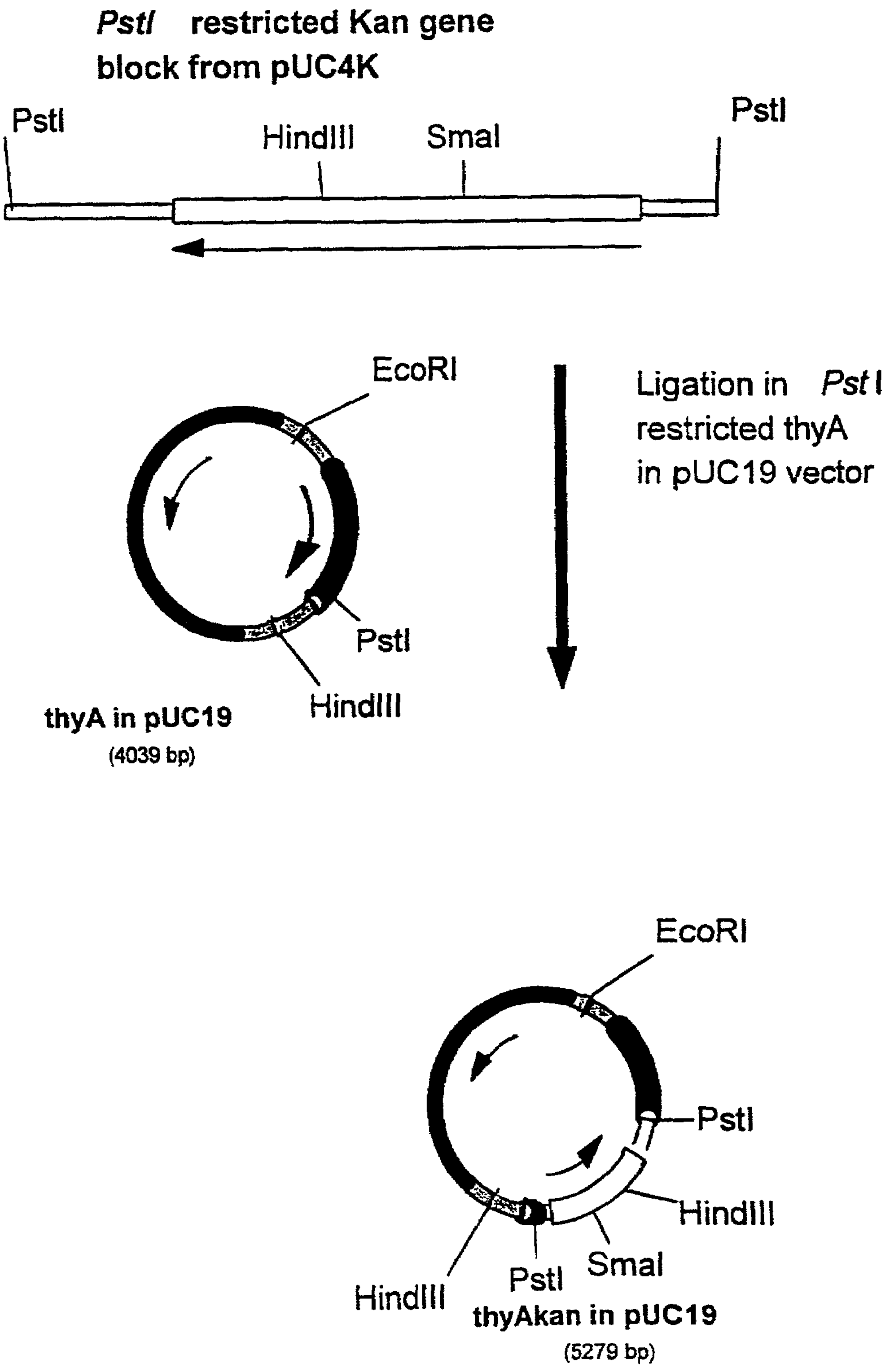

FIG. 8 shows the insertion of a $Kan^R$-resistance gene block in the PstI site of the *V. cholerae* thyA gene in pUC19.

Figure 9:
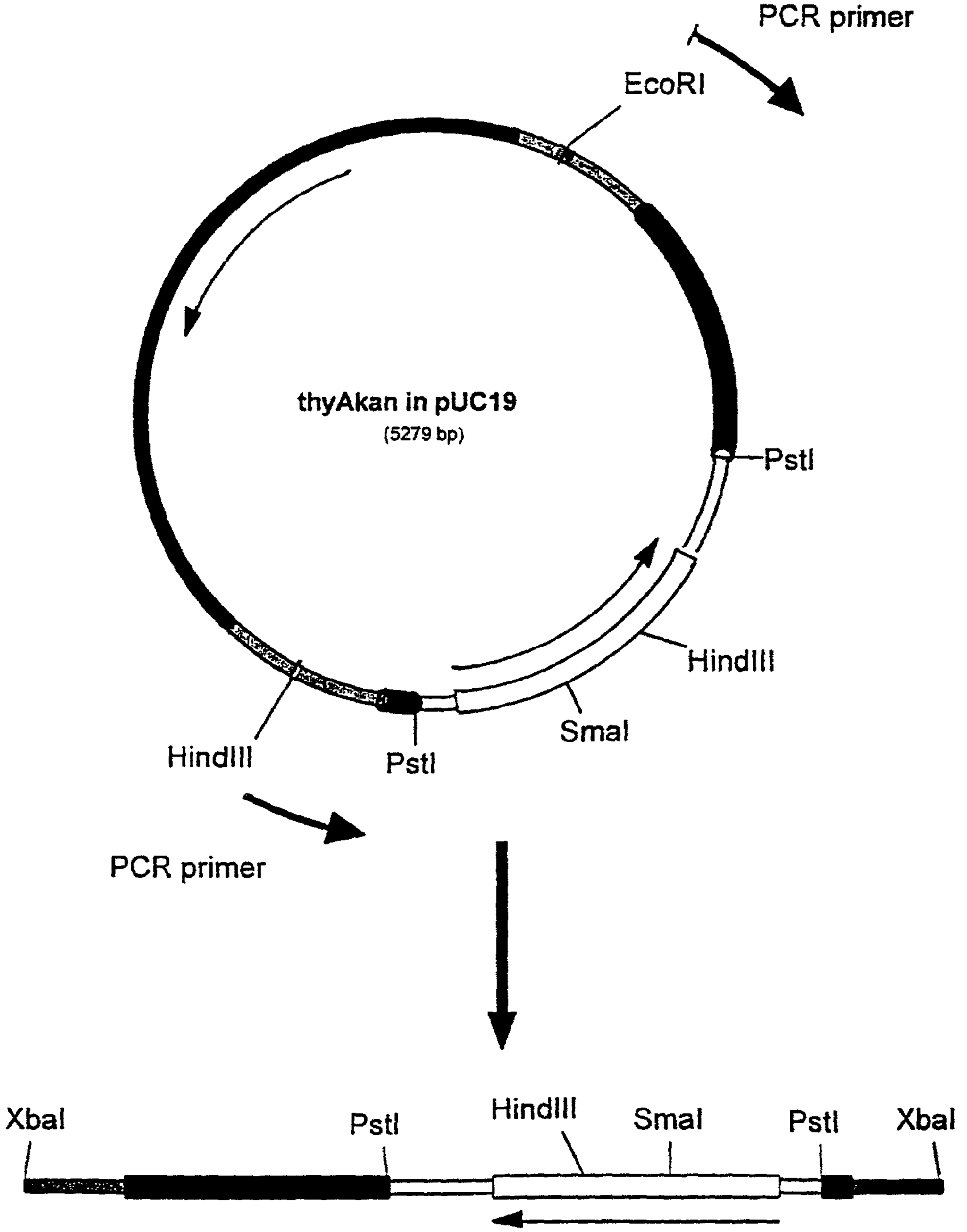

FIG. 9 shows PCR to generate a thyA-Kan fragment with XbaI ends.

Figure 10:
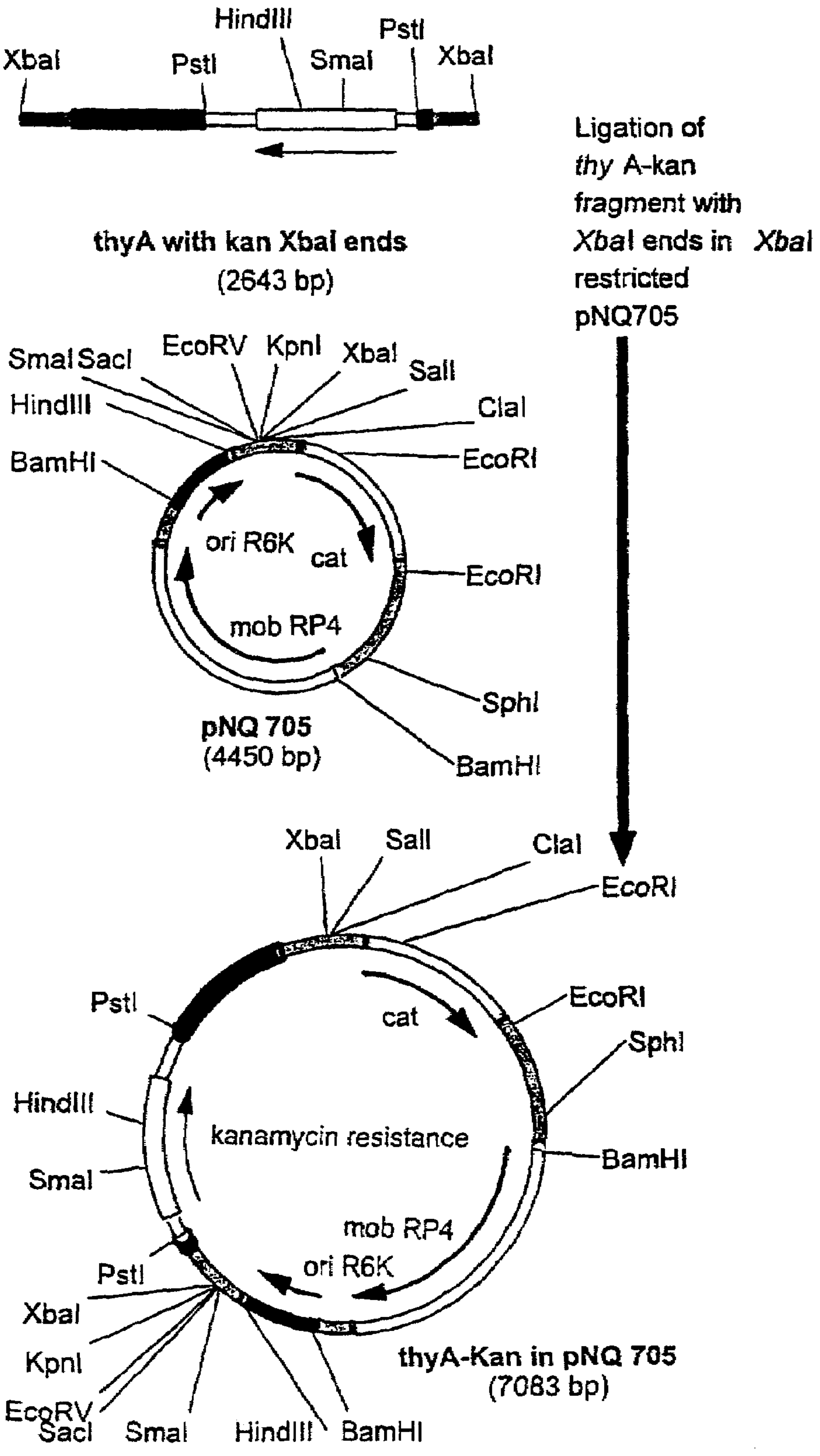

FIG. 10 shows ligation of the thyA-Kan fragment with XbaI ends in plasmid pNQ705.

Figure 11:
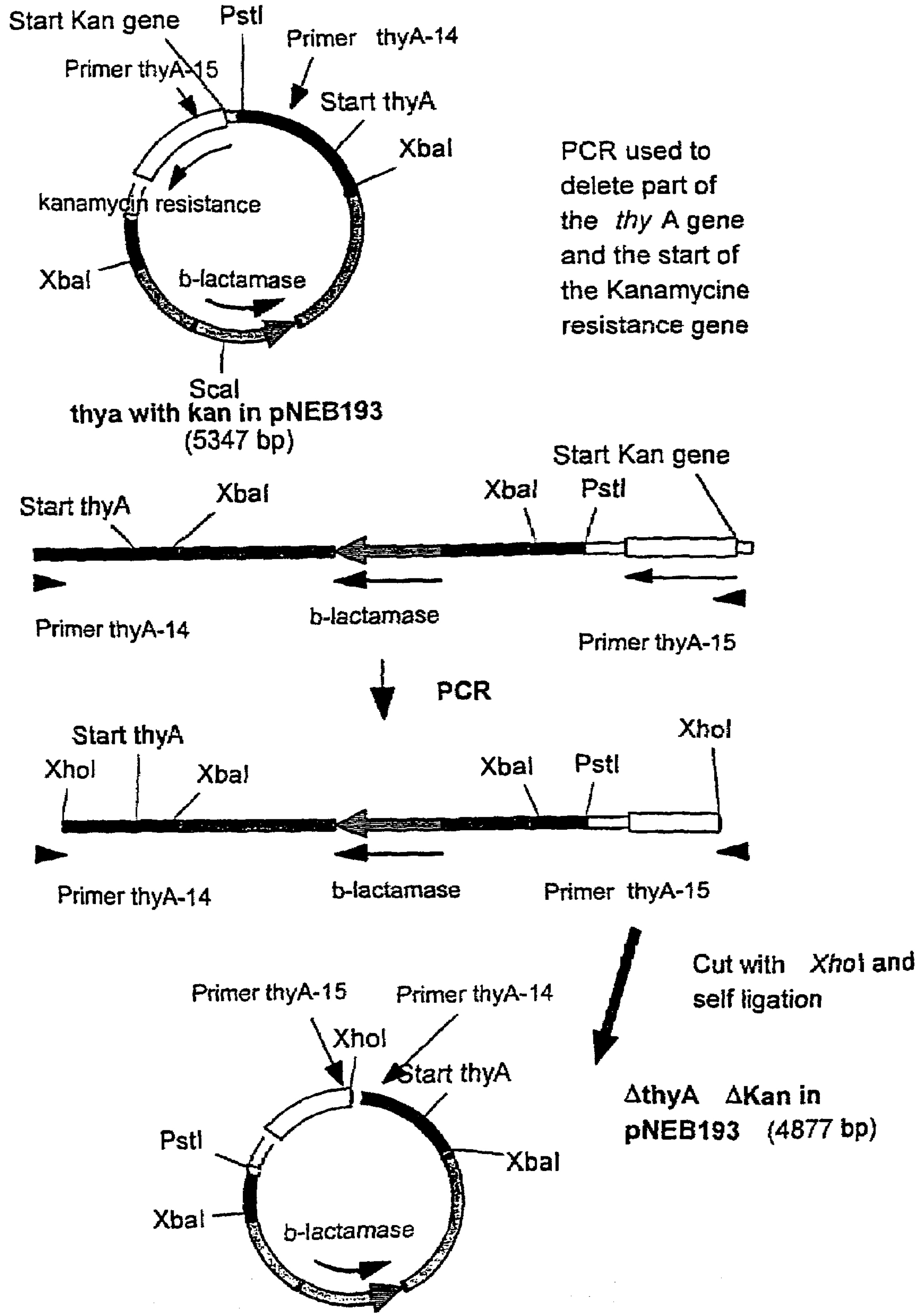

FIG. 11 shows partial deletion of the thyA gene and the start of the Kan gene in pNEB193.

Figure 12:
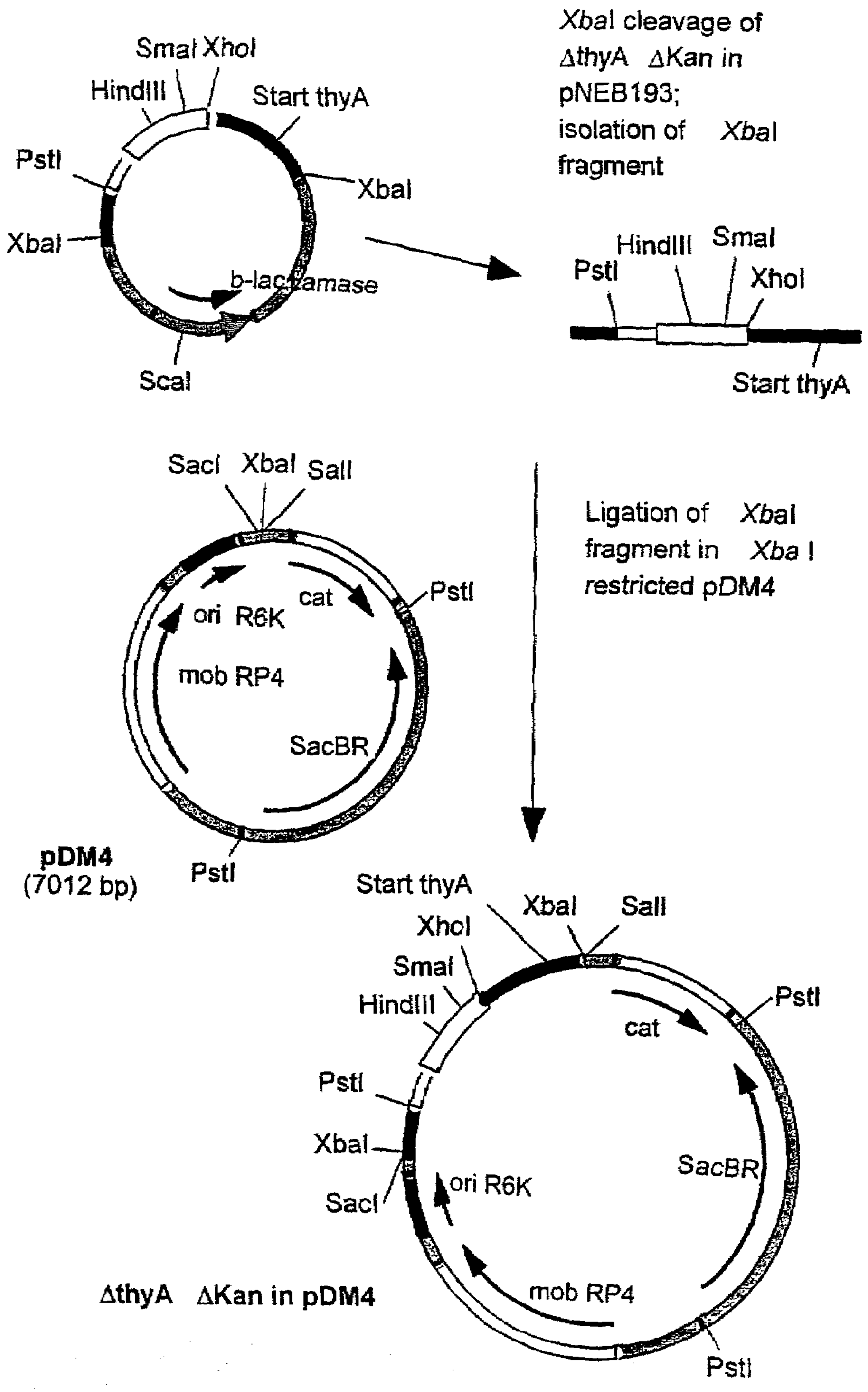

FIG. 12 shows XbaI cleavage to excise the ΔthyA Δkan gene from pNEB193, ligation into XbaI restricted pDM4.

Figure 13:
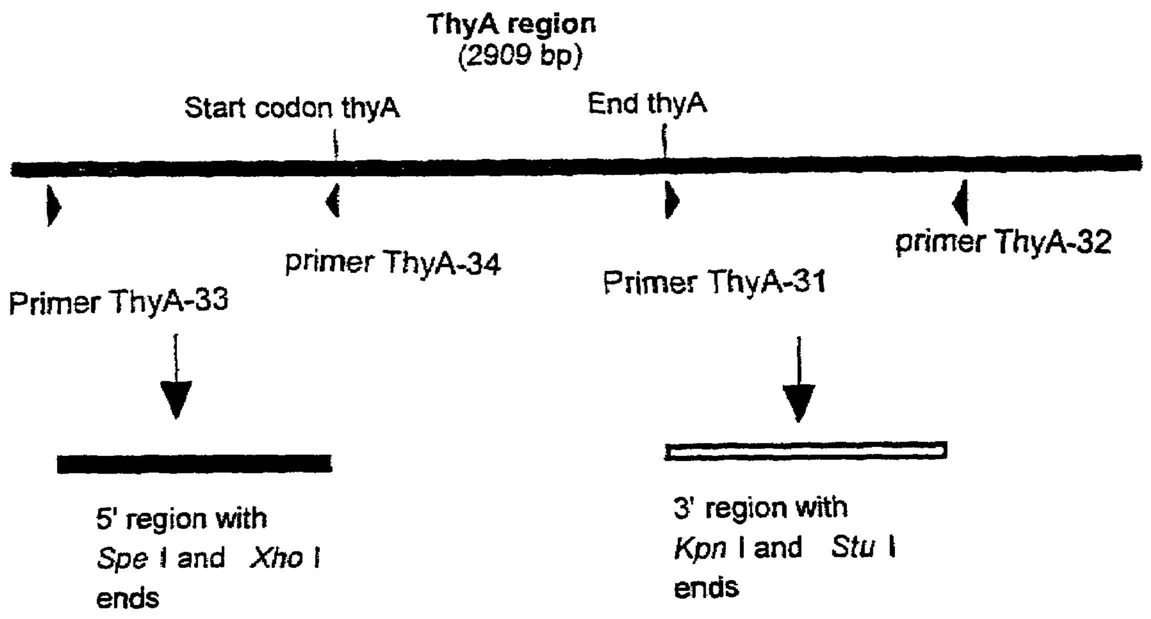

FIG. 13 shows an outline of a strategy to completely delete the thyA gene of *V. cholerae.*

Figure 14:
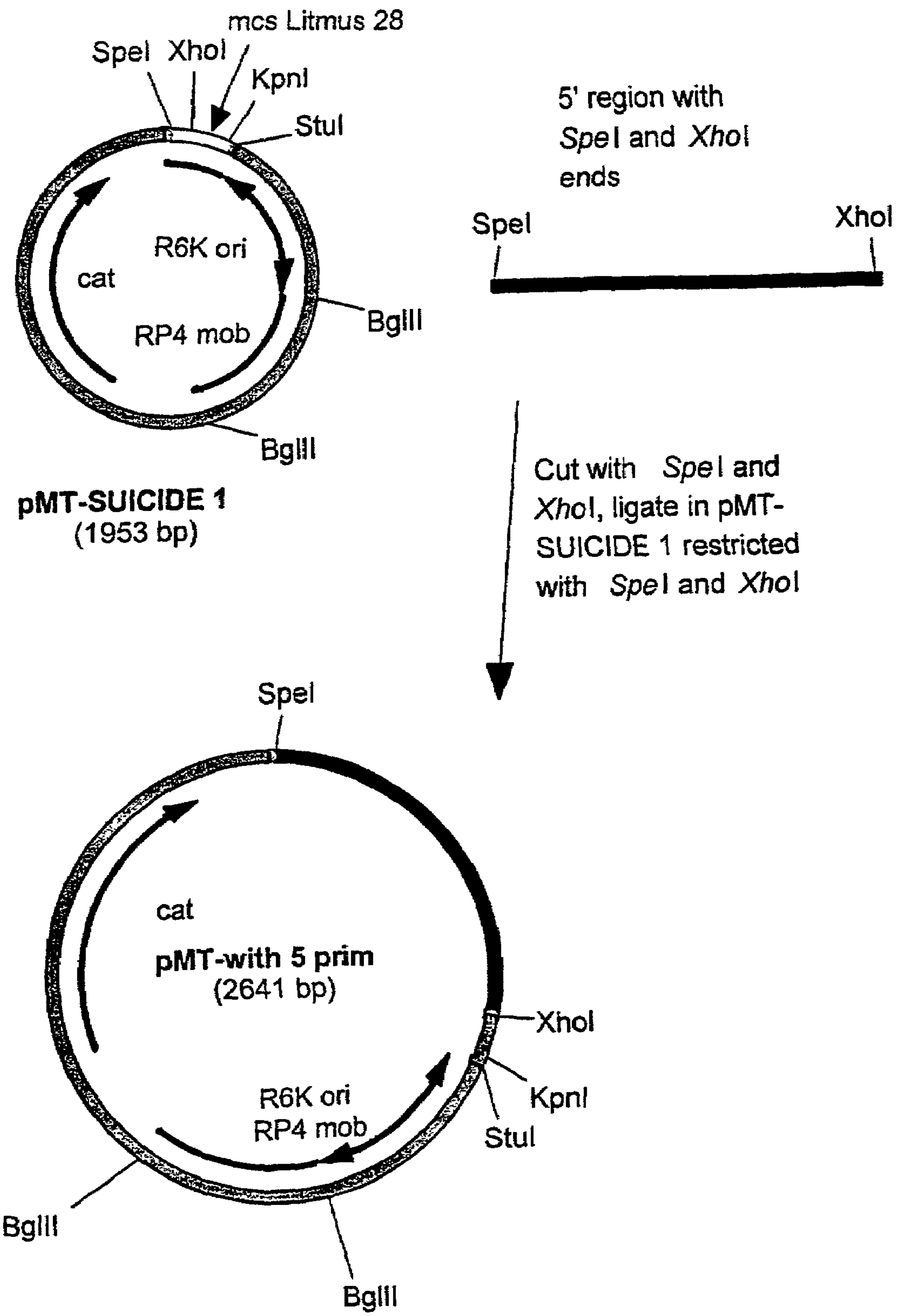

FIG. 14 shows insertion of the 5' region upstream of thyA in pMT-SUICIDE 1; generation of pMT with 5 prim.

Figure 15:
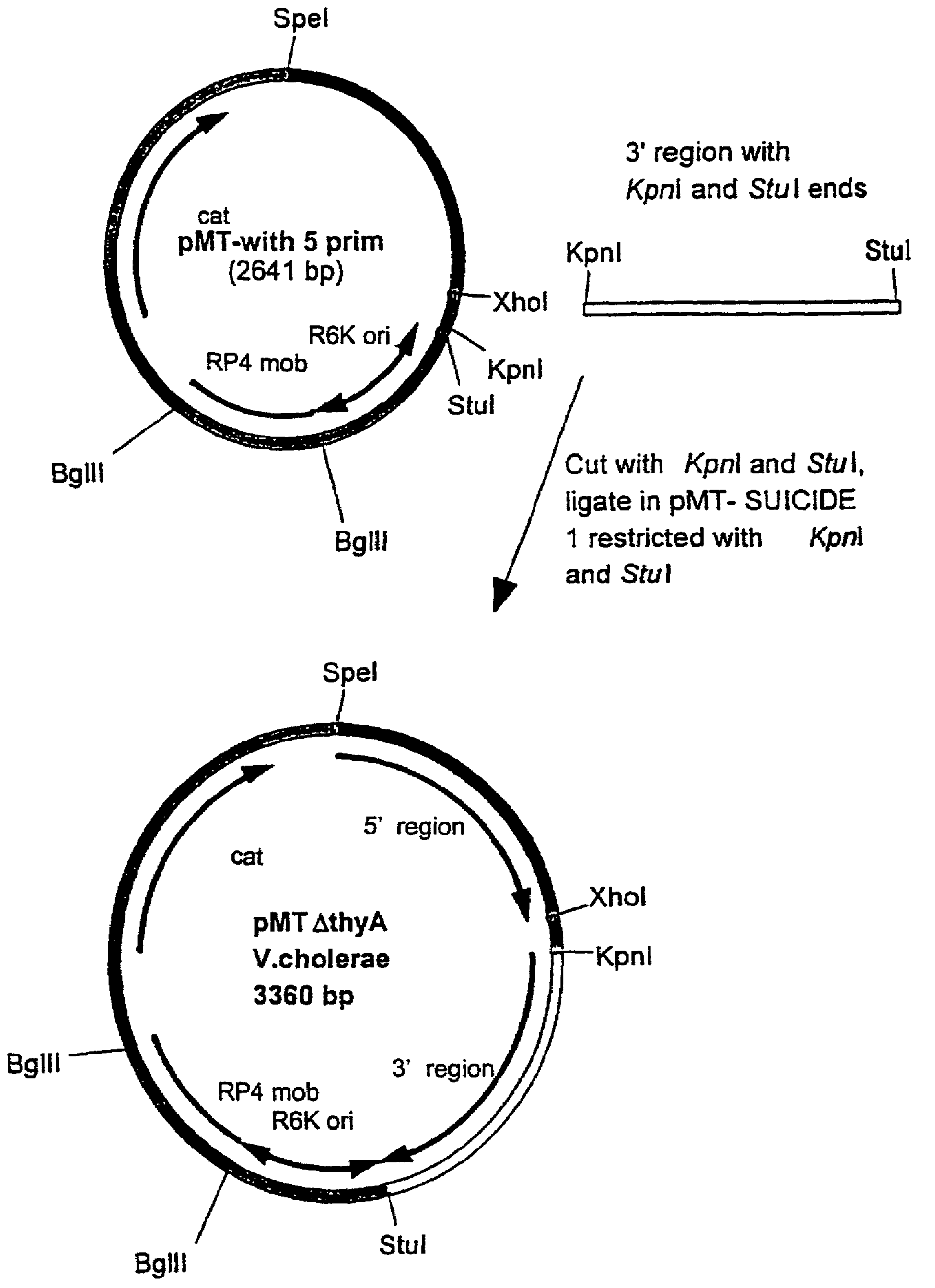

FIG. 15 shows insertion of the 3' region downstream of thyA in pMT with 5 prim; generation of pMT ΔthyA *V. cholerae.*

Figure 16:
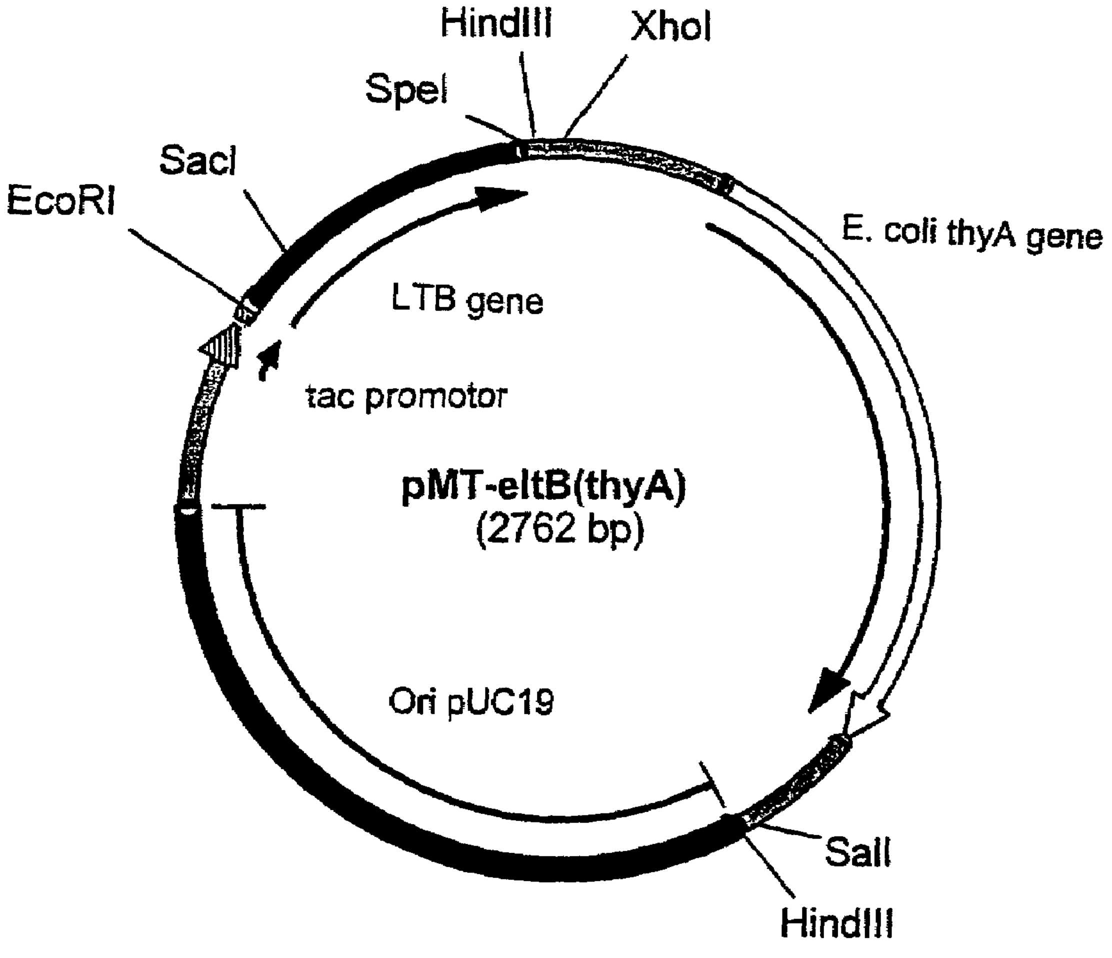

FIG. 16 shows the expression vector pMT-eltB(thyA) used for expression of LTB in *V. cholerae* JS1569 ΔthyA.

Figure 17:
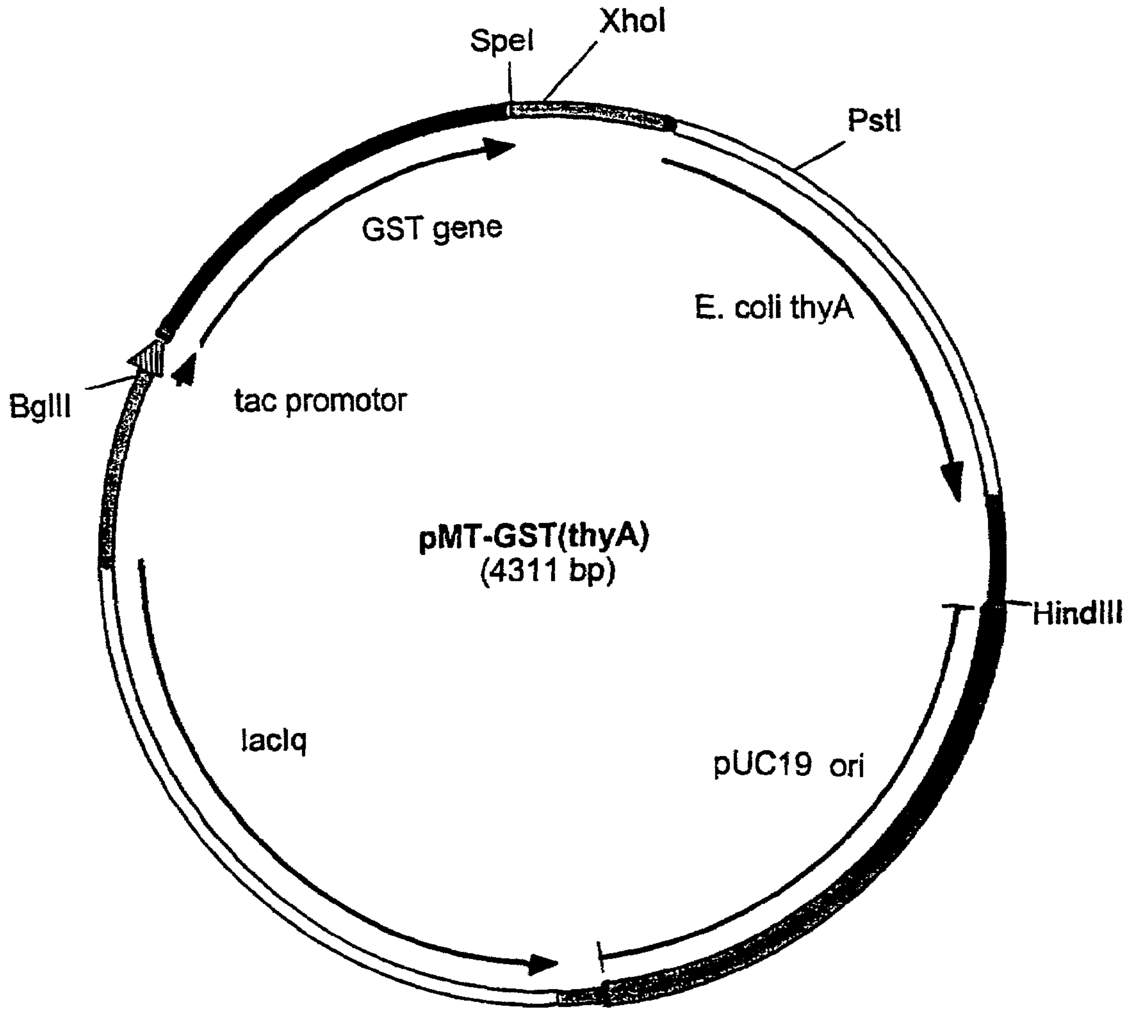

FIG. 17 shows the expression vector pMT-GST(thyA) used for expression of GST in *V. cholerae* JS1569 ΔthyA.

DESCRIPTION OF EXPERIMENTS

Strategy Employed

In order to produce defined thyA mutants of *V. cholerae* that could be used as suitable production strains for recombinant proteins encoded on plasmids maintained by thyA complementation, it was first necessary to clone and characterise the wild-type gene and its 5' and 3' flanking regions. Our strategy was to first clone the thyA gene of *V. cholerae* on a plasmid, on the basis of complementation of the thyA auxotrophy in a strain of *E. coli* K12. Restriction analysis and subcloning experiments were done in order to locate the thyA structural gene on the large DNA fragment initially obtained. The appropriate region containing the thyA gene and it's 5' and 3' flanking regions gene was then sequenced.

To verify that one of the sequenced genes was in fact the thyA gene of *V. cholerae*, homology comparisons were made with thyA sequences from other organisms. The cloned gene could also complement the thyA phenotype of a *V. cholerae* mutant strain that had been selected on the basis of trimethoprim resistance. Sequence analysis of this mutant showed that it did indeed have a single base change in the gene we had identified as thyA, which resulted in a stop codon giving a non-functional truncated gene product.

Knowledge of the thyA sequence and that of the region surrounding it allowed the use of suitable suicide vectors for site-directed mutagenesis. Strategies considered were (a) insertional inactivation (b) a combination of insertional inactivation and gene deletion and (c) removal of the entire gene:

(a) Insertional inactivation of the thyA gene was achieved by insertion of a $Kan^R$ gene block (with the suicide vector pNQ705 [14].

(b) A deletion of approximately 400 bp was made in the strain carrying the $Kan^R$ geneblock that removed 200 bp each from the thyA gene upstream of the insertion site and from the kanamycin resistance gene which was thereby inactivated. We thus obtained a deleted thyA gene where the deletion was in the central part of the gene and followed by an insertion of a non-coding region of DNA. This construct was inserted into the *V. cholerae* chromosome using the suicide vector pDM4 and resulted in a strain called JS1569 ΔthyAΔKan.

(c) Complete removal of the thyA gene was done by ligating together the regions flanking the structural gene, taking care not to disrupt other open reading-frames (disruption of the adjacent lgt gene is also lethal). The DNA carrying the deletion was cloned into a novel suicide vector (PMT-SUICIDE-1) used for insertion of the sequence into the *V. cholerae* chromosome. The resulting strain is called JS1569 ΔthyA.

For expression of recombinant genes in these ΔthyA strains of *V. cholerae*, two expression vectors were constructed. Each consisted of the thyA gene from *E. coli*, the origin of replication of the general purpose high copy-number vector pUC19, the tac promotor and the rho-independent trpA transcription terminator. In one of the two vectors the $lacI^q$ gene had been inserted in order to regulate expression from the tac promotor which also contained the lac operator sequence.

Two genes were cloned into these plasmids and expressed in the newly generated thyA-deleted strain of *V. cholerae*; JS1569ΔthyA. The first encoded the B subunit of human heat-labile enterotoxin from *E. coli* (LTB) (FIG. 16), the second was the sj26 glutathione-S-transferase (GST) from *Schistosoma japonicum* (FIG. 17).

LTB is similar in structure to the B subunit of cholera toxin naturally produced by the host strain and was secreted into the growth medium. The other protein is eukaryotic in origin, coming from the Asian Liver Fluke. Sj26 GST is known to express to high levels in *E. coli* and accumulates in the cytoplasm. Expression of the two recombinant proteins was assessed on the basis of GM1 ELISA of the culture supernatant in the case of LTB and a commercially available assay in the case of GST. Both proteins were also analysed on the basis of SDS-PAGE and Western blots.

Origin of the thyA Gene

The thyA gene was cloned from strain *V. cholerae* JS 1569. This strain originates from the *V. cholerae* Inaba strain 569B of the classical biotype (ATCC No 25870). The strain has a deletion in the ctxA gene [7] and has been made rifampicin resistant [8].

Cloning of a 1.4 kB HindIII/EcoRI Fragment Encompassing the *V. cholerae* thyA Gene.

Chromosomal DNA prepared by the CTAB method [9] was digested to completion with the restricion enzyme HindIII.

The digested DNA was ligated into the general purpose vector plasmid pBR322 (New England Biolabs Inc. Beverly, Mass. USA) which had been digested with HindIII and treated with alkaline phosphatase.

The ligation mixture was electroporated [10] into a *E. coli* HB101 strain that was phenotypically $ThyA^-$ (selected on the basis of trimethoprim resistance) and the culture spread onto modified Syncase (MS) agar plates [11] supplemented with 50 μg/ml ampicillin, but containing no thymine. Thus transformants were selected both on the basis of plasmid acquisition and the presence of a functional thyA gene.

Colonies that grew up were streaked out to single colonies on the same type of agar plates, and then grown up in MS broth supplemented with ampicillin. Plasmid DNA was prepared by "Wizard miniprepps" (ProMega Corp. Madison Wis.) and digested with HindIII. A fragment of approx. 10-12 kB was isolated, this clone was named ThyA B2.

To reduce the size of the fragment, the plasmid was cut with EcoRI and religated using T4 ligase. The ligated DNA was again electroporated into the *E. coli* strain described above using the same selective conditions for growth of transformants.

Figure 6:
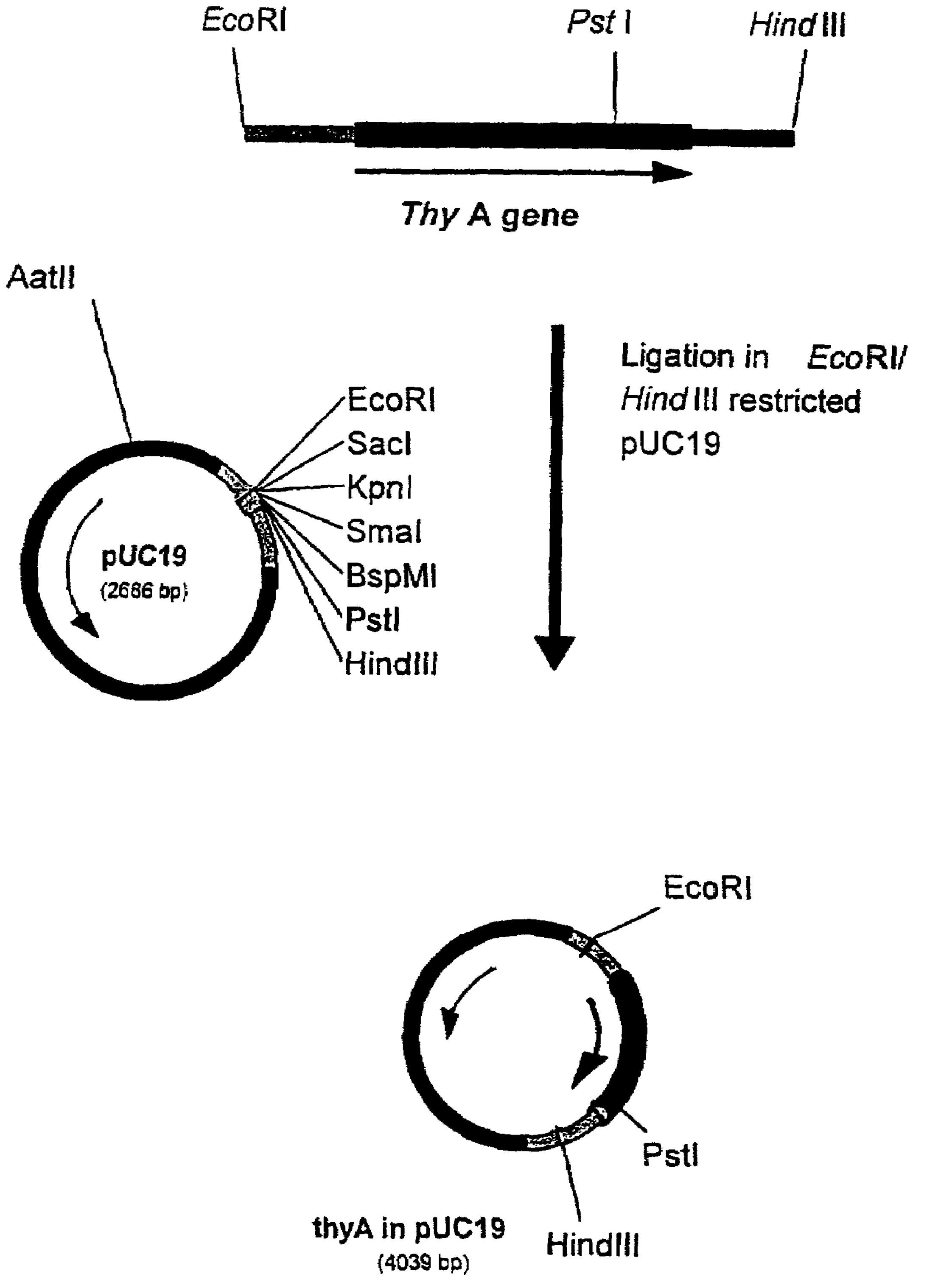
FIG. 6 shows the cloning of a EcoRI/HindIII fragment containing the *V. cholerae* thyA gene in pUC19.

Colonies resulting from this experiment were isolated as described above and plasmid DNA purified and analysed by double digest with EcoRI and HindIII. A DNA fragment of approximately 1.4 kb remained which retained the ability to complement the thyA mutation in the *E. coli* host strain. This fragment was cloned into the plasmid pUC19 (New England Biolabs) that had been digested with the same two enzymes and treated with alkaline phosphatase. Following electroporation, transformants from the experiment were isolated and characterised as described above. This clone was called ThyA 1:2 (FIG. 6).

Verification that the 1.4 kB HindIII/EcoRI Fragment Contains the thyA Gene.

Southern blot analysis. To verify that the cloned fragment was indeed from *V. cholerae* chromosomal origin, DNA from strain JS1569 was digested to completion with HindIII and EcoRI and HindIII. The DNA fragments were resolved by agarose electrophoresis together with HindIII digested clone ThyA B2 and EcoRI and HindIII digested clone ThyA 1:2.

After electrophoresis the DNA was transferred to a Nylonmembrane, immobilised by UV irradiation and hybridised (under stringent conditions) with the 1.5 kB fragment excised from clone ThyA 1:2 that had been labelled with $^{32}P$ dCTP using Amershams Multiprime kit.

Results. In both HindIII digested chromosomal DNA and in HindIII digested clone ThyA B2 an approx. 10 kB band was evident. Likewise in EcoRI/HindIII digested chromosomal DNA and clone ThyA 1:2 plasmid DNA a 1.4 kB band was evident (data not shown). These data demonstrated that the cloned fragment was derived from *V. cholerae* JS1569 DNA.

Transformation of JS1569 $ThyA^-$ with the Plasmid ThyA 1:2.

To verify that the 1.4 B cloned EcoRI/HindIII fragment could support growth of phentotypically $ThyA^-$ *V. cholerae*, a thymine dependent mutant of JS1569 (*V. cholerae* JS1569 4.4) was electroporated with the plasmid ThyA 1:2. Electroporation and selective media were as described above. JS1569 4.4 does not grow on MS medium without the addition of thymine.

Results. Colonies of JS1569 4.4 were isolated that grew in the absence of thymine. All were shown to harbour the ThyA 1:2 plasmid, thus supporting the assumption that the cloned fragment contained the thyA gene from *V. cholerae.*

DNA sequencing of the plasmid ThyA 1:2. Plasmid DNA was sequenced by the dideoxy chain termination method [12] using the ABI PRISM™ Dye terminator cycle sequencing kit (Perkin Elmer). Both commercially available as well as custom made primers were used. The DNA sequences were analysed on an ABI PRISM 373 automatic sequencer (Perkin Elmer). Data were analysed using the AutoAssembler Software package (Perkin Elmer). Homology searches with the found DNA sequence were done with the GCG program [13].

Results. The best homologies were with thymidylate synthetases from various species. Note that the homology with *E. coli* thymidylate synthetase is rather weak. (FIG. 7)

Strategy for Deletion of the thyA Gene in *V. cholerae* JS1569.

Two different strategies were used for obtaining defined thyA mutants of *V. cholerae* JS1569, the first involved inactivation of the thyA gene by insertion of a $Kan^R$ gene block followed by partial deletion of the thyA gene and the $Kan^R$ gene block. The second strategy was directed to completely delete the thyA gene from the chromosome by means of a novel suicide vector pMT SUICIDE-1. This vector contains the 5' and 3' flanking regions of the thyA gene as well as the R6K origin of replication and the RP4 mob genes.

To replace the thyA gene of strain JS1569 we decided to use the already thymine-dependent JS1569 4.4 since preliminary experiments indicated that there is a strong selective disadvantage to go from wildtype to thymine dependence even in the presence of high levels of exogeneous thymine.

Inactivation of the thyA Gene by Insertion of a $Kan^R$ Gene Block

Our strategy involved inactivation of the thyA gene by insertion of a kanamycin resistance gene into a unique PstI site in the thyA gene in the form of a $Kan^R$ gene block (Pharmacia) (FIG. 8). This construct was amplified by PCR (Expand™High Fidelity PCR system Boehringer Mannheim) with primers that incorporate XbaI ends so that it could be transferred into the suicide plasmid pNQ705 [14] which carries a unique XbaI site and the chloramphenicol resistance gene.

The following primers were used for PCR amplification of the insertionally inactivated gene:

```
                                     (SEQ ID NO:8)
ThyA-10: 5'GCT CTA GAG CCT TAG AAG GCG TGG TTC3'
```

corresponding to bases 557 to 575 in SEQ ID NO:2 (FIG. 2) with an added XbaI site (in bold)

and

```
ThyA-11:                             (SEQ ID NO:9)
5'GCT CTA GAG CTA CGG TCT TGA TTT ACG GTA T3'
```

corresponding to the complementary sequence of bases 235 to 257 in SEQ ID NO:2 (FIG. 3) with an added XbaI site (in bold) (FIGS. 9+10)

The resulting plasmid was then transferred to the *E. coli* S-17 that was used in conjugation experiments.

Since the recipient strain JS1569 4.4 is rifampicin resistant and chloramphenicol sensitive and the donor strain *E. coli* S-17 is both chloramphenicol and kanamycin resistant, transconjugants were selected by selection for resistance to both rifampicin and kanamycin.

The resulting *V. cholerae* strains however would also be chloramphenicol resistant since the entire plasmid would initially be inserted into the chromosome.

Exconjugants that had incorporated the inactivated thyA gene carrying the $Kan^R$ geneblock into the chromosome and lost the pNQ705 plasmid could then be selected among those that were chloramphenicol sensitive but remained kanamycin resistant.

To verify insertion of the Kanamycin resistance gene in the thyA gene the entire thyA gene was PCR amplified with primers thyA-10 and thyA-11, and the size of the resulting fragment compared to that of the native thyA gene. The expected thyA fragment of 2.6 kb compared to that of the native thyA gene of 1.4 kb was found.

Results. Exconjugants were shown to be kanamycin resistant, chloramphenicol sensitive and when amplified by PCR, shown to have incorporated the kanamycin resistance gene block into the chromosome. Sequencing of the amplified fragment showed that the only defect in the gene was due to the insertion of the kanamycin gene. This indicated that the recombination event that had incorporated the insertionally inactivated gene into the chromosome had also eliminated the point mutation that had made the recipient strain (JS1569 4.4) thymine dependent. Growth of the resulting strain was only observed if the growth medium was supplemented with thymine (200 μg/ml).

Partial Deletion of the thyA Gene and the $Kan^R$ Gene Block

To further ensure a nonreversible thyA mutation the insertionally inactivated thyA was subcloned as a XbaI fragment into pNEB 193 (New England Biolabs). PCR primers were designed that deleted 209 basepairs from the thyA gene and removed 261 basepairs from the $Kan^R$ geneblock.

Thus the thyA gene was further disrupted and the kanamycin resistance gene was also inactivated (by removal of the start of the coding region). The overall result of this procedure was a strain carrying a deleted thyA gene that also contained an insertion of noncoding DNA.

```
                                     (SEQ ID NO:10)
ThyA-14: 5'GGG GGC TCG AGG GGC ACA TCA CAT GAA3'
                                     (SEQ ID NO:11)
ThyA-15: 5'CCC CCC TCG AGC GCC AGA GTT GTT TCT GAA3'
Letters in bold indicate XhoI cleavage sites (FIG.
11).
```

After PCR amplification a DNA fragment was obtained encompassing the entire plasmid with exception of the deleted region. The amplified DNA was digested with XhoI, self ligated and transformed into *E. coli* HB101. Colonies were selected for on plates containing ampicillin. Individual colonies were selected and restreaked. Small-scale plasmid preparations from individual colonies yielded the expected restriction patterns when analysed with XbaI, XhoI, HindIII and RsaI restriction enzymes.

The incomplete thyA gene carrying an inactivated kanamycin resistance gene was cut out from the vector by XbaI digestion, purified and ligated into pDM4 [15] (FIG. 12). PDM4 is a suicide vector derived from pNQ705 containing the SacBR gene from *Bacillus subtilis* and a modified multicloning site.

After transfer of the pDM4 (ΔthyAΔKan) plasmid to the *E. coli* S-17 strain a transconjugation experiment was performed. This time the *V. cholerae* JS1569 thyAKan strain obtained above was used as recipient strain.

The mating was done as described above with selection for rifampicin and chloramphenicol. After growth in this medium colonies were selected on medium containing 10% sucrose in the absence of chloramphenicol. Sucrose induces the sacBR gene which encodes levansucrase that converts sucrose to levan. This compound is toxic to many Gram negative organisms. In this way clones still carrying the suicide plasmid were killed leaving exconjugants that had lost the plasmid.

Results. A colony was selected that was chloramphenicol and kanamycin sensitive. PCR amplification of the thyA region with the primers ThyA-10 and thyA-11 confirmed that the thyAKan fragment (2.6 kb) on the chromosome had been replaced with the ΔthyAΔKan fragment (2.1 kb).

Growth of the resulting strain was only observed if the growth medium was supplemented with thymine (200 μg/ml). This strain was named *V. cholerae* JS1569 ΔthyAΔKan.

Direct Deletion of the thyA Gene in *V. cholerae*.

For this approach the 5' and 3' sequences flanking the thyA gene were used. A novel suicide vector was constructed, pMT SUICIDE-1 (FIG. 14) that contains the R6K origin of replication, the mob genes from RP4, a chloramphenicol resistance gene and a multicloning site from Litmus 28 (New England Biolabs). Effectively, a modified fragment was constructed in which the thyA coding region was replaced by a multicloning site (derived from Litmus 28) leaving only the 5' and 3' region of the thyA locus from *V. cholerae*. The resulting plasmid was used to generate a *V. cholerae* strain in which the entire thyA gene had been deleted.

As starting material for this construction the pMT SUICIDE-1 plasmid was used (M. Lebens, unpublished).

From the 5' and 3' regions of the thyA locus the following PCR primers were designed:

(SEQ ID NO:12)
ThyA-33: $^{5'}$GGA CTA GTG GGT TTC CTT TTT GCT AT$^{3'}$ corresponding to bases 109 to 126 in the SEQ ID NO:2 (FIG. 2) (5' region of the thyA region) with a SpeI site (indicated in bold) and (SEQ ID NO:13)
ThyA-34: $^{5'}$CCC CGC TCG AGA CCC TAT TTT GCT GCT AC$^{3'}$ corresponding to the complementary sequence of base 815 to 832 in the SEQ ID NO:2 with a XhoI site (indicated in bold) attached to it.

This primer pair gives a PCR fragment of 743 bases corresponding to the 5' flanking region of the thyA gene.

(SEQ ID NO:14)
ThyA-31: $^{5'}$CGG GGT ACC TGG CTT GAT GGG TTT TAT$^{3'}$ corresponding to bases 22 to 39 in the SEQ ID NO:3 (FIG. 3) (3' region of the thyA region) with a KpnI site (indicated in bold) and (SEQ ID NO:15)
ThyA-32: $^{5'}$GAA GGC CTT CGC CTC TGC TTG CGA CT$^{3'}$ corresponding to the complementary sequence of bases 731 to 749 in the SEQ ID NO:3 with a StuI site (indicated in bold)

This primer pair gives a PCR fragment of 746 bases corresponding to the 3' flanking region of the thyA gene.

As template for the PCR reactions a chromosomal DNA preparation from *V. cholerae* JS1569 was used (FIG. 13).

The amplified DNA were digested with the appropriate restriction enzymes and cloned into the pMT-SUICIDE 1 vector (FIGS. 14 and 15) yielding the plasmid pMTΔthyA *V. cholerae* that contains approximately 700 base-pairs of the 5' region upstreams of the thyA gene and the same number of base-pairs of the 3' region downstreams of the thyA gene.

This plasmid was transferred to *E. coli* S17-1 and used in conjugation experiments as described above. As recipient the *V. cholerae* JS1569 4.4 strain was used. Matings were done on LB agar supplemented with rifampicin, chloramphenicol and thymine. Exconjugants that had lost the suicide plasmid from the chromosome were selected on the basis of chloramphenicol sensitivity.

Results. A chloramphenicol sensitive and rifampicin resistant colony was selected. PCR amplification with the primers ThyA-10 and ThyA-11 of the thyA region resulted in a 1.4 kb fragment from the native thyA gene and a 0.6 kb fragment from the ΔthyA gene. This confirmed that the thyA structural gene on the chromosome had been deleted. Furthermore the bacteria could only grow in medium complemented with thymine. This strain is named *V. cholerae* JS1569 ΔthyA.

Expression of the B Subunit of Heat-Labile Enterotoxin from *E. coli* (LTB) and the sj26 Glutathione-S-Transferase (GST) from *Schistosoma japonicum* in *V. cholerae* JS1569 ΔthyA.

Two expression vectors were constructed, each consisted of the thyA gene from *E. coli*, the origin of replication of the high copy-number vector pUC19, the tac promotor and the rho-independent trpA transcription terminator. In one of the two vectors the lacI$^q$ gene had been inserted in order to regulate expression from the tac promotor which also contained the lac operator sequence (FIGS. 16 and 17).

Expression of the LTB Protein in *V. cholerae* JS1569 ΔthyA Strain.

The expression vector shown in FIG. 16 was electroporated into *V. cholerae* JS1569 ΔthyA. Transformants were selected for on MS-agar. Individual colonies were grown up to produce mini-plasmid preps that were checked by restriction enzyme analysis. For expression a transformant was grown in MS medium at 37° C. in a shaker culture. The culture medium was harvested and assayed for LTB by the GM1-ELISA.

Results. The culture was found to produce approximately 300 μg/ml of LTB as assayed by the GM1 ELISA. SDS-PAGE and Western blot using an LTB specific monoclonal antibody further verified that the secreted protein was LTB.

Expression of the GST Protein in *V. cholerae* JS1569 ΔthyA Strain

The sj26 glutathione-S-transferase (GST) from *Schistosoma japonicum* was cloned in the expression vector shown in FIG. 17. This vector is identical to the first except for the sequence of the lacI$^q$ gene. The lacI$^q$ allows for controlled expression of recombinant proteins. The vector was electroporated into *V. cholerae* JS1569 ΔthyA. Transformants were selected for on MS-agar. Individual colonies were grown up to produce mini-plasmid preps that were checked by restriction enzyme analysis. For expression a transformant was grown in MS medium at 37° C. in a shaker culture with addition of IPTG.

Results. The recombinant protein was found in the cytoplasm of the *V. cholerae* bacteria. SDS-PAGE and Western blot with a GST specific monoclonal antibody (Pharmacia BioTech, Uppsala) confirmed that GST was expressed. The level of GST expression was more difficult to determine than for LTB since the protein was expressed intracellulary but was judged to be in the same range as for LTB.

REFERENCES

1. Molin, S., K. A. Gerdes. 1984. Stabilized plasmids. U.S. Pat. No. 4,760,022.
2. Morona, R., and S. R. Attridge. 1987. Non-antibiotic marker system. EPC-A-0251579.
3. Green, J. M., B. P. Nichols, and R. G. Matthews. 1996. Folate biosynthesis, reduction and polyglutamylation. In: F. C. Neidhardt, R. Curtiss III, J. L. Ingraham, E. C. C. Lin, K. B. Low, B. Magasanik, W. S. Reznikoff, M. Riley, M. Schaechter and H. E. Umbarger (Eds.) *Escherichia coli* and *Salmonella* cellular and molecular biology. ASM Press Washington D.C. pp 665-673.
4. Neill, R. J., B. E. Ivins, and R. K. Holmes. 1983. Synthesis and secretion of the plasmid-coded heat-labile enterotoxin of *Escherichia coli* in *Vibrio cholerae*. Science. 221: 289-290.
5. Sandkvist, M., M. Bagdasarian, S. P. Howard, and V. J. DiRita. 1995. Interaction between the autokinase EpsE and EpsL in the cytoplasmic membrane is required for extracellular secretion in *Vibrio cholerae*. EMBO J. 14:1664-1673.
6. Neuhard, J. and R. A. Kelln. 1996. Biosynthesis and conversions of pyrimidines. In: F. C. Neidhardt, R. Curtiss III, J. L. Ingraham, E. C. C. Lin, K. B. Low, B. Magasanik, W. S. Reznikoff, M. Riley, M. Schaechter and H. E. Umbarger (Eds.) *Escherichia coli* and *Salmonella* cellular and molecular biology. ASM Press Washington D.C. pp 580-599.
7. Kaper, J. B., H. Lockman, M. M. Baldini, and M. M. Levine. 1984. A recombinant live oral cholera vaccine. Biotechnology 2:345-349.
8. Sanchez, J., and J. Holmgren. 1989. Recombinant system for overexpression of cholera toxin B subunit in *Vibrio cholerae* as a basis for vaccine development. Proc. Natl. Acad. Sci. USA. 86:481-485.
9. Wilson, K. 1994. Preparation of genomic DNA from Bacteria. In Current protocols in Molecular Biology (F. A. Ausubel, R. Brent, R. E. Kingston, D. D. Moore, J. G. Seidman, J. A. Smith, and K. Struhl, eds.) pp. 2.4.1-2.4.2 John Wiley & Sons, New York.
10. Sheen, J. 1994. High-efficiency transformation by electroporation. In Current protocols in Molecular Biology (F. A. Ausubel, R. Brent, R. E. Kingston, D. D. Moore, J. G. Seidman, J. A. Smith, and K. Struhl, eds.) pp. 1.8.4-1.8.5. John Wiley & Sons, New York.
11. Lebens, M., S. Johansson., J. Osek., M. Lindblad and J. Holmgren. 1993. Large-scale production of *Vibrio cholerae* toxin B subunits for use in oral vaccines. Biotechnology. 11:1574-1578.
12. Sanger, F., S. Nicklen, and A. R. Coulson. 1977. DNA sequencing with chain-terminating inhibitors. Proc. Natl. Acad. Sci. USA 74:5463-5467.
13. Program Manual for the Wisconsin Package. Version 8. September 1994. Genetics Computer Group, 575 Science Drive, Madison Wis.
14. Milton, D. L., A. Nordqvist, and H. Wolf-Watz. 1992. Cloning a metalloprotease gene involved in the virulence mechanism of *Vibrio anguillarum* J. Bacteriol. 174:7235-7244.
15. Milton, D. L., R. O'Toole, P. Högstedt, and H. Wolf-Watz. 1996. Flagellin A is essential for the virulence of *Vibrio anguillarum* J. Bacteriol. 176:1310-1319.
16. Belfort, M., G. Maley, J. Pedersen-Lane and F. Maley. 1983. Primary tructure of the *Escherichia coli* thyA gene and its thymidylate synthase product. Proc. Natl. Acad. Sci. USA 80: 4914-4918.
17. Fleischmann, R. D., Adams, M. D., White, O., Clayton, R. A., Kirkness, E. F., Kerlavage, A. R., Bult, C. J., Tomb, J. -F., Dougherty, B. A., Merrick, J. M., McKenney, K., Sutton, G., FitzHugh, W., Fileds, C. A., Gocayne, J. D., Scott, J. D., Shirely, R., Liu, L. -I., Glodek, A., Kelley, J. M. Weidman, J. F., Phillips, C. A., Spriggs, T., Hedblom, E., Cotton, M. D., Utterback, T. R., Hanna, M. C., Nguyen, D. T., Saudek, D. M., Brandon, R. C., Fine, L. D., Fritchman, J. L., Fuhrmann, J. L., Geoghagen N. S. M., Gnehm, C. L., McDonald, L. A., Small, K. V., Fraser, C. M., Smith, H. O., and J. C. Venter. 1995. Whole-genome random sequencing and assembly of *Haemophilus influenzae* RD. Science 269:496-512.

The invention claimed is:

1. A ΔthyA strain of *Vibrio cholerae* lacking the functionality of its thyA gene located in the chromosome of said strain due to site-directed deletion and/or insertion of nucleotides in the thyA gene, said thyA gene consisting of the nucleotide sequence of SEQ ID NO: 1.

2. The ΔthyA strain of *Vibrio cholerae* of claim 1, wherein said strain comprises at least one episomal autonomously replicating DNA element having a functional thyA gene that enables the strain to grow in the absence of thymine in a growth medium, wherein the at least one episomal autonomously replicating DNA element further comprises a structural gene encoding a homologous or heterologous protein.

3. The ΔthyA strain of *Vibrio cholerae* of claim 2, wherein the at least one episomal autonomously replicating DNA element is a plasmid.

4. The ΔthyA strain of *Vibrio cholerae* of claim 2, wherein the functional thyA gene is a foreign thyA gene.

5. The ΔthyA strain of *Vibrio cholerae* of claim 4, wherein the foreign thyA gene is *Escherichia coli* thyA gene.

6. The ΔthyA strain of *Vibrio cholerae* of claim 2, wherein the encoded heterologous protein is selected from the group consisting of heat-labile enterotoxin B-subunit of *Escherichia coli* (LTB) and *Schistosoma japonicum* glutathione S-transferase 26 kD protein (GST 26 kD).

7. The ΔthyA strain of *Vibrio cholerae* of claim 1, wherein the insertion is of a kanamycin resistance gene into pstI site in the thyA gene in the form of a $Kan^R$ geneblock.

8. The ΔthyA strain of *Vibrio cholerae* of claim 7, wherein 209 base pairs from said thyA gene upstream of the insertion site and 261 basepairs from the $Kan^R$ geneblock have been deleted.

* * * * *